United States Patent
Ozaki et al.

(10) Patent No.: US 6,812,229 B1
(45) Date of Patent: Nov. 2, 2004

(54) CARBAMATE DERIVATIVE AND AGRICULTURAL/HORTICULTURAL FUNGICIDE

(75) Inventors: Masami Ozaki, Shizuoka (JP); Shunichiro Fukumoto, Shizuoka (JP); Ryuji Tamai, Shizuoka (JP); Kazuhiro Ikegaya, Fujieda (JP); Norihisa Yonekura, Shizuoka (JP); Takahiro Kawashima, Kashiwa (JP); Junetsu Sakai, Shizuoka (JP); Norimichi Muramatsu, Kakegawa (JP); Makikazu Takagaki, Shizuoka (JP); Kouzou Nagayama, Kakegawa (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 139 days.

(21) Appl. No.: 10/048,925

(22) PCT Filed: Aug. 3, 2000

(86) PCT No.: PCT/JP00/05225

§ 371 (c)(1),
(2), (4) Date: Feb. 5, 2002

(87) PCT Pub. No.: WO01/10825

PCT Pub. Date: Feb. 15, 2001

(30) Foreign Application Priority Data

Aug. 5, 1999 (JP) .......................................... 11/221896

(51) Int. Cl.⁷ ..................... C07C 271/20; C07C 275/24; C07D 213/74; C07D 215/14; A01N 47/12

(52) U.S. Cl. .................... 514/238.8; 546/330; 546/174; 514/357; 514/407; 514/471; 514/256; 514/438; 514/365; 514/311; 514/241; 514/274; 514/475; 514/367; 514/252.1; 514/521; 514/485; 549/452; 549/483; 549/77; 549/553; 544/335; 544/168; 544/316; 544/219; 544/336; 548/204; 548/167; 558/388; 558/391; 560/24

(58) Field of Search ................................. 546/330, 174; 514/357, 467, 471, 256, 438, 365, 311, 238.8, 274, 475, 241, 367, 252.1, 521, 485; 549/452, 483, 77, 553; 544/335, 168, 316, 219, 336; 548/204, 167; 558/388, 391; 560/24

(56) References Cited

FOREIGN PATENT DOCUMENTS

JP 9-507218 7/1997

OTHER PUBLICATIONS

Patent Abstract of Hungary, 1 page, HU 192750, Jul. 28, 1987.
Patent Abstract of Hungary, 2 pages, HU 196105, Oct. 28, 1988.
Patent Abstract of Hungary, 4 pages, HU P9401961 (217905), Aug. 28, 1995.
I.D. Kersey et al.: "Photoactivatable Analogues of a SubstanceP Non–Peptidic Antagonist, for Probing the Antagonist Binding Site of the NK1 Receptor" Bioorg. Med. Chim. Lett., vol. 5, No. 12, pp. 1271–1274.

*Primary Examiner*—Richard L. Raymond
*Assistant Examiner*—Hong Liu
(74) *Attorney, Agent, or Firm*—Oblon, Spivak, McClelland, Maier & Neustadt, P.C.

(57) ABSTRACT

It is to provide a novel fungicide having high controlling effects on plant diseases particularly on wheat powdery mildew and cucumber gray mold, without ill effects on crops.

A carbamate derivative represented by the general formula [I]

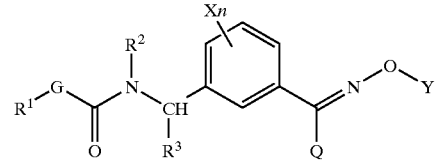

{wherein X is a halogen atom, a $C_1$–$C_6$ alkyl group or the like, n is 0 or an integer of from 1 to 4, $R^1$ is a $C_1$–$C_6$ alkyl group, $R^2$ is a hydrogen atom, a $C_1$–$C_6$ alkyl group or the like, $R^3$ is a hydrogen atom or a $C_1$–$C_6$ alkyl group, G is an oxygen atom, a sulfur atom or the like, Y is a hydrogen atom, a $C_1$–$C_{10}$ alkyl group, $C_2$–$C_{10}$ alkenyl group or the like, and Q is a hydrogen atom, a $C_1$–$C_6$ haloalkyl group, a phenyl group or the like} and an agricultural/horticultural fungicide containing the same as the active ingredient.

13 Claims, No Drawings

CARBAMATE DERIVATIVE AND AGRICULTURAL/HORTICULTURAL FUNGICIDE

TECHNICAL FIELD

The present invention relates to a novel carbamate derivative and an agricultural/horticultural fungicide containing said derivative as the active ingredient.

BACKGROUND ART

Heretofore, many carbamic acid derivatives have been reported, but it has not been known that a carbamic acid derivative having an oxime ether group in a phenyl group as the compound of the present invention has excellent fungicidal activities.

The object of the present invention is to provide a novel carbamate derivative and an agricultural/horticultural fungicide containing the same as the active ingredient.

DISCLOSURE OF THE INVENTION

The present inventors have conducted extensive studies to produce a novel agricultural/horticultural fungicide and as a result, have found that the carbamate derivative of the present invention (hereinafter referred to as compound of the present invention) is a novel compound not disclosed in any literatures and have outstanding effects as an agricultural/horticultural fungicide, and have finally accomplished the present invention. Namely, the present invention resides in (1) a carbamate derivative represented by the general formula [I]:

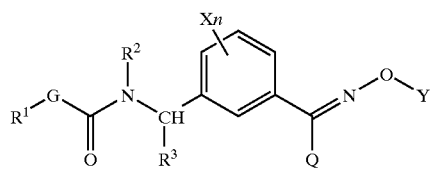

{wherein X is a halogen atom, a $C_1$–$C_6$ alkyl group, a $C_1$–$C_6$ alkoxy group, a $C_1$–$C_6$ haloalkyl group or a $C_1$–$C_6$ haloalkoxy group, n is 0 or an integer of from 1 to 4, $R^1$ is a $C_1$–$C_6$ alkyl group, $R^2$ is a hydrogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $C_1$–$C_6$ alkylcarbonyl group, a $C_1$–$C_6$ alkoxycarbonyl group, a $C_1$–$C_6$ alkylcarbonyl $C_1$–$C_6$ alkyl group or a benzyl group which may be substituted, $R^3$ is a hydrogen atom or a $C_1$–$C_6$ alkyl group, G is an oxygen atom, a sulfur atom or a —$NR^4$— group [wherein $R^4$ is a hydrogen atom or a $C_1$–$C_6$ alkyl group], Y is a hydrogen atom, a $C_1$–$C_{10}$ alkyl group (said group may be substituted by the same or different at least one halogen atom, cyano group, nitro group, hydroxyl group, $C_3$–$C_6$ cycloalkyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ alkylsulfinyl group, carboxyl group, $C_1$–$C_6$ alkylcarbonyl group, $C_1$–$C_6$ alkoxycarbonyl group, $C_1$–$C_6$ alkoxyimino group or C(O)$NR^5R^6$ (wherein each of $R^5$ and $R^6$ which are the same or different, is a hydrogen atom or a $C_1$–$C_6$ alkyl group)), a $C_2$–$C_{10}$ alkenyl group (said group may be substituted by the same or different at least one halogen atom, cyano group, nitro group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or C(O)$NR^5R^6$ (wherein each of $R^5$ and $R^6$ which are the same or different, is a hydrogen atom or a $C_1$–$C_6$ alkyl group)), a $C_2$–$C_{10}$ alkynyl group (said group may be substituted by the same or different at least one halogen atom, cyano group, nitro group, cycloalkyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or C(O)$NR^5R^6$ (wherein each of $R^5$ and $R^6$ which are the same or different, is a hydrogen atom or a $C_1$–$C_6$ alkyl group)), a $C_3$–$C_6$ cycloalkyl group (said group may be substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or C(O)$NR^5R^6$ (wherein each of $R^5$ and $R^6$ which are the same or different, is a hydrogen atom or a $C_1$–$C_6$ alkyl group)), a $C_3$–$C_6$ cycloalkenyl group (said group may be substituted by the same or different at least one halogen atom, cyano group, nitro group, $C_1$–$C_6$ alkyl group, $C_2$–$C_6$ alkenyl group, hydroxyl group, $C_2$–$C_6$ alkynyl group, amino group, mono $C_1$–$C_6$ alkylamino group, di-$C_1$–$C_6$ alkylamino group, $C_1$–$C_6$ alkoxy group, $C_1$–$C_6$ alkylthio group, $C_1$–$C_6$ haloalkyl group, $C_1$–$C_6$ alkylcarbonyl group, $C_1$–$C_6$ alkoxycarbonyl group or C(O)$NR^5R^6$ (wherein each of $R^5$ and $R^6$ which are the same or different, is a hydrogen atom or a $C_1$–$C_6$ alkyl group)), a phenacyl group (said group may be substituted by the same or different at least one halogen atom, $C_1$–$C_6$ alkyl group, $C_1$–$C_6$ alkoxy group, $C_1$–$C_6$ haloalkyl group, $C_1$–$C_6$ alkylcarbonyl group or $C_1$–$C_6$ alkoxycarbonyl group), an aryl group (said group may be substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or C(O)$NR^5R^6$ (wherein each of $R^5$ and $R^6$ which are the same or different, is a hydrogen atom or a $C_1$–$C_6$ alkyl group)), a heteroaryl group (said group may be substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or C(O)$NR^5R^6$ (wherein each of $R^5$ and $R^6$ which are the same or different, is a hydrogen atom or a $C_1$–$C_6$ alkyl group)), an aryl-$C_1$–$C_6$ alkyl group (the aryl in said group may be substituted by the same or different at least one halogen atom, cyano group, nitro group, $C_1$–$C_6$ alkyl group, $C_2$–$C_6$ alkenyl group, $C_2$–$C_6$ alkynyl group, phenoxy group which may be substituted, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ haloalkoxy group, $C_1$–$C_6$ alkylcarbonyl group, $C_1$–$C_6$ alkoxycarbonyl group, $C_1$–$C_6$ alkoxyimino $C_1$–$C_6$ alkyl group or C(O)$NR^5R^6$ (wherein each of $R^5$ and $R^6$ which are the same or different, is a hydrogen atom or a $C_1$–$C_6$ alkyl group)), an aryl-$C_2$–$C_6$ alkenyl group (the aryl in said group may be substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or $C(O)NR^5R^6$ (wherein each of $R^5$ and $R^6$ which are the same or different, is a hydrogen atom or a $C_1$–$C_6$ alkyl group)) or a heterocyclic-$C_1$–$C_6$ alkyl group (the heterocycle in said group may be substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or $C(O)NR^5R^6$ (wherein each of $R^5$ and $R^6$ which are the same or different, is a hydrogen atom or a $C_1$–$C_6$ alkyl group)), and Q is a hydrogen atom, a haloalkyl group, a cyano group, a $C_1$–$C_6$ alkyl group, a $C_3$–$C_6$ cycloalkyl group, a $C_1$–$C_4$ alkylthio group, a $C_1$–$C_4$ alkylsulfinyl group, a $C_1$–$C_4$ alkylsulfonyl group or a phenyl group (said group may be substituted by at least one halogen atom, cyano group, nitro group, $C_1$–$C_4$ alkyl group, $C_2$–$C_4$ alkenyl group, $C_2$–$C_4$ alkynyl group, hydroxyl group, $C_1$–$C_4$ alkoxy group, $C_1$–$C_4$ haloalkyl group, $C_1$–$C_4$ haloalkoxy group, $C_1$–$C_4$ alkylcarbonyl group or $C_1$–$C_4$ alkoxycarbonyl group)}, and (2) an agricultural/horticultural fungicide containing the same as the active ingredient.

Symbols and terms used in the present specification will be explained.

The halogen atom is a fluorine atom, a chlorine atom, a bromine atom or an iodine atom.

A notation such as $C_1$–$C_{10}$ indicates that the carbon number of a substituent following this notation is from 1 to 10 in this case.

The $C_1$–$C_6$ alkyl group is a straight chain or branched chain alkyl group and may, for example, be methyl, ethyl, n-propyl, iso-propyl, n-butyl, iso-butyl, sec-butyl, tert-butyl, n-pentyl, iso-pentyl, neopentyl, n-hexyl, 1,1-dimethylpropyl or 1,1-dimethylbutyl.

The $C_1$–$C_{10}$ alkyl group may, for example, be the above-mentioned $C_1$–$C_6$ alkyl group, or a group such as heptyl, octyl, 1,1-diethylbutyl, nonyl or decyl.

The $C_3$–$C_6$ cycloalkyl group may, for example, be a group such as cyclopropyl, cyclobutyl, cyclopentyl or cyclohexyl.

The $C_3$–$C_6$ cycloalkenyl group may, for example, be a group such as 1-cyclopenten-1-yl, 2-cyclopenten-1-yl, 1-cyclohexen-1-yl or 2-cyclohexen-1-yl.

The $C_1$–$C_6$ haloalkyl group is a straight chain or branched chain alkyl group substituted by a halogen atom and may, for example, be a group such as fluoromethyl, chloromethyl, difluoromethyl, dichloromethyl, trifluoromethyl or pentafluoroethyl.

The $C_2$–$C_{10}$ alkenyl group is a straight chain or branched chain alkenyl group and may, for example, be vinyl, 1-propenyl, 2-propenyl, isopropenyl, 1-butenyl, 2-butenyl, 1-hexenyl or 1-octenyl.

The $C_2$–$C_{10}$ alkynyl group is a straight chain or branched chain alkynyl group and may, for example, be a group such as ethynyl, 1-propynyl, 2-propynyl, 1-butynyl, 2-butynyl, 3-butynyl, 4-methyl-1-pentynyl or 3-methyl-1-pentynyl.

The $C_1$–$C_6$ alkoxy group is an alkyloxy group wherein the alkyl moiety has the above meaning and may, for example, be a group such as methoxy, ethoxy, n-propoxy, isopropoxy, n-butoxy, isobutoxy, sec-butoxy, tert-butoxy, n-pentyloxy, isopentyloxy or n-hexyloxy.

The $C_1$–$C_6$ haloalkoxy group is a haloalkyloxy group wherein the haloalkyl moiety has the above meaning and may, for example, be a group such as fluoromethoxy, difluoromethoxy, trifluoromethoxy or pentafluoroethoxy.

The $C_1$–$C_6$ alkoxyimino group is an alkoxyimino group wherein the alkoxy moiety has the above meaning and may, for example, be a group such as methoxyimino.

The $C_1$–$C_6$ alkoxyimino $C_1$–$C_6$ alkyl group is an alkoxyiminoalkyl group wherein the alkoxy moiety and the alkyl moiety have the above meanings and may, for example, be a group such as 1-methoxyiminoethyl.

The $C_1$–$C_6$ alkylcarbonyl group is an alkylcarbonyl group wherein the alkyl moiety has the above meaning, and may, for example, be a group such as acetyl, propionyl, butyryl, isobutyryl, pivaloyl or hexanoyl.

The $C_1$–$C_6$ alkoxycarbonyl group is an alkoxycarbonyl group wherein the alkoxy moiety has the above meaning and may, for example, be a group such as methoxycarbonyl, ethoxycarbonyl, isopropoxycarbonyl or hexyloxycarbonyl.

The $C_1$–$C_6$ alkylcarbonyl $C_1$–$C_6$ alkyl group is an alkylcarbonylalkyl group wherein the alkyl moiety has the above meaning and may, for example, be a group such as a 2-oxypropyl group, a 3-oxobutyl group, a 3-oxopentyl group or a 3,3-dimethyl-2-oxobutyl group.

The aryl group is an aromatic hydrocarbon group and may, for example, be a group such as phenyl, 1-naphthyl or 2-naphthyl.

The heterocyclic-$C_1$–$C_6$ alkyl group is a 3- to 10-membered cycle wherein the alkyl moiety is —$CH_2$—, —$CH_2CH_2$—, —$CH_2CH_2CH_2$—, —CH(Me)—, —C(Me)$_2$—, —CH(Et)— or the like, and the heterocyclic moiety is constituted of from 2 to 9 carbon atoms, from 0 to 3 nitrogen atoms, from 0 to 3 oxygen atoms and from 0 to 3 sulfur atoms, and may, for example, be a group such as pyrrolyl, furyl, thienyl, pyrazolyl, isoxazolyl, isothiazolyl, imidazolyl, oxazolyl, thiazolyl, pyridyl, pyridazinyl, pyrimidinyl, pyrazinyl, triazinyl, indolyl, benzofuryl, benzothienyl, benzimidazolyl, benzoxazolyl, benzothiazolyl, quinolyl, isoquinolyl, morpholino, oxyranyl or dioxacyclopentyl.

The heteroaryl group is a 5- to 10-membered heterocyclic aromatic ring group constituted of from 2 to 9 carbon atoms, from 0 to 3 nitrogen atoms, from 0 to 3 oxygen atoms and from 0 to 3 sulfur atoms, and may, for example, be a heterocycle such as pyrrolyl, furyl, thienyl, pyrazolyl, isoxazolyl, isothiazolyl, imidazolyl, oxazolyl, thiazolyl, pyridyl, pyridazinyl, pyrimidinyl, pyrazinyl, triazinyl, indolyl, benzofuryl, benzothienyl, benzimidazolyl, benzoxazolyl, benzothiazolyl, quinolyl or isoquinolyl.

The $C_1$–$C_6$ alkoxy $C_1$–$C_6$ alkyl group is a group wherein the alkyl moiety and the alkoxy moiety have the above meanings and may, for example, be a group such as methoxymethyl, ethoxymethyl, isopropoxymethyl, pentyloxymethyl, methoxyethyl or butoxyethyl.

The mono $C_1$–$C_6$ alkylamino group is a group wherein the alkyl moiety has the above meaning and may be a group such as methylamino, ethylamino, isopropylamino, butylamino or tert-butylamino.

The di-$C_1$–$C_6$ alkylamino group is a group wherein each of the alkyl moieties which are the same or different, has the above meaning, and may, for example, be a group such as dimethylamino, diethylamino, methylethylamino, methylisopropylamino or dihexylamino.

The $C_1$–$C_6$ alkylthio group is a group wherein the alkyl moiety has the above meaning and may be a group such as methylthio, ethylthio, isopropylthio, butylthio or hexylthio.

The $C_1$–$C_6$ alkylsulfinyl group is a group wherein the alkyl moiety has the above meaning and may be a group such as methylsulfinyl, ethylsulfinyl, isopropylsulfinyl, butylsulfinyl or hexylsulfinyl.

The $C_1$–$C_6$ alkylsulfonyl group is a group wherein the alkyl moiety has the above meaning and may be a group such as methylsulfonyl, ethylsulfonyl, isopropylsulfonyl, butylsulfonyl or hexylsulfonyl.

The aryl $C_1$–$C_6$ alkyl group is a group wherein the aryl moiety has the above meaning and the alkyl moiety is —CH$_2$—, —CH$_2$CH$_2$—, —CH$_2$CH$_2$CH$_2$—, —CH(Me)—, —C(Me)$_2$—, —CH(Et)— or the like.

The aryl $C_1$–$C_6$ alkenyl group is a group wherein the aryl moiety has the above meaning and the alkenyl moiety is —CH=CH—, —CH=CHCH$_2$—, —C(Me)=CH—, —CH(Et)=(CH)—, —C(Me)=CHCH$_2$— or the like.

The heteroaryl $C_1$–$C_6$ alkyl group is a group wherein the heteroaryl moiety has the above meaning and the alkyl moiety is —CH$_2$—, —CH$_2$CH$_2$—, —CH$_2$CH$_2$CH$_2$—, —CH(Me)—, —(Me)$_2$—, —CH(Et)— or the like.

BEST MODE FOR CARRYING OUT THE INVENTION

Now, specific examples of the compound of the present invention represented by the general formula [I] will be described in Tables 1 to 13. However, the compound of the present invention is not limited to such compounds. Here, the compound Nos. will be referred to in the subsequent description.

Symbols in the Tables have the following meanings respectively. Me represents a methyl group, Et represents an ethyl group, Pr represents a n-propyl group, Pr-i represents an iso-propyl group, Bu represents a n-butyl group, Bu-i represents an iso-butyl group, Bu-s represents a sec-butyl group, Bu-t represents a tert-butyl group, Hex represents a n-hexyl group, Pr-c represents a cyclopropyl group, Pen-c represents a cyclopentyl group, Hex-c represents a cyclohexyl group, and Ph represents a phenyl group. Further, Ph(4-Cl) represents a 4-chlorophenyl group for example.

Some of the compounds of the present invention represented by the general formula [I] have one or from 2 to 3 double bonds relating to E/Z isomers in their molecules, and with respect to such compounds, E/Z isomer mixtures are present. Pure individual E-forms and Z-forms and their mixtures are also included in the compounds of the present invention. The following pairs of compounds are geometrical isomers relating to oxime portion double bond (A-80 and A-206, A-84 and A-207, A-85 and A-208, A-86 and A-209, A-286 and A-448).

TABLE 1

| Comp. No. | G | $R^1$ | $R^2$ | $R^3$ | $X^1$ | $X^2$ | $X^3$ | $X^4$ | Q | Y | m.p.(° C.) or RI($n_D^{20}$) |
|---|---|---|---|---|---|---|---|---|---|---|---|
| A-1 | O | Me | H | H | H | H | H | H | CN | Me | 84–87 |
| A-2 | O | Me | H | H | Cl | H | H | H | CN | H | 1.5601 |
| A-3 | O | Me | H | H | Cl | H | H | H | CN | Me | 104–107 |
| A-4 | O | Me | H | H | Cl | H | H | H | CN | CH$_2$CH=CH$_2$ | |
| A-5 | O | Me | H | H | Cl | H | H | H | CN | CH$_2$C≡CH | |
| A-6 | O | Me | H | H | Cl | H | H | H | CN | CH$_2$COOEt | |
| A-7 | O | Me | H | H | Cl | H | H | H | CN | CH$_2$Ph | 113–115 |
| A-8 | O | Me | H | H | Cl | H | H | H | CN | CH$_2$Ph(2-Cl) | 115–118 |
| A-9 | O | Me | H | H | Cl | H | H | H | CN | CH$_2$Ph(3-Cl) | 127–130 |
| A-10 | O | Me | H | H | Cl | H | H | H | CN | CH$_2$Ph(4-Cl) | |
| A-11 | O | Me | H | H | Cl | H | H | H | CN | CH$_2$Ph(2-Me) | 113–116 |
| A-12 | O | Me | H | H | Cl | H | H | H | CN | CH$_2$Ph(3-Me) | |
| A-13 | O | Me | H | H | Cl | H | H | H | CN | CH$_2$Ph(4-Me) | |
| A-14 | O | Me | H | H | Cl | H | H | H | CN | CH$_2$Ph(2-CF$_3$) | |
| A-15 | O | Me | H | H | Cl | H | H | H | CN | CH$_2$Ph(3-CF$_3$) | |
| A-16 | O | Me | H | H | Cl | H | H | H | CN | CH$_2$Ph(4-CF$_3$) | |
| A-17 | O | Me | H | H | Cl | H | H | H | CN | Me | |
| A-18 | O | Me | H | H | Cl | H | H | H | CN | Et | |
| A-19 | O | Me | H | H | Cl | H | H | H | CN | CH$_2$CH=CH$_2$ | |
| A-20 | O | Me | H | H | Me | H | H | H | CN | CH$_2$Ph | 104–107 |
| A-21 | O | Me | H | H | Me | H | H | H | CN | CH$_2$Ph(2-Cl) | 120–123 |
| A-22 | O | Me | H | H | Me | H | H | H | CN | CH$_2$Ph(3-Cl) | |
| A-23 | O | Me | H | H | Me | H | H | H | CN | CH$_2$Ph(4-Cl) | |
| A-24 | O | Me | H | H | Me | H | H | H | CN | CH$_2$Ph(2-Me) | |
| A-25 | O | Me | H | H | Me | H | H | H | CN | CH$_2$Ph(3-Me) | |
| A-26 | O | Me | H | H | Me | H | H | H | CN | CH$_2$Ph(4-Me) | |
| A-27 | O | Me | H | H | Me | H | H | H | CN | CH$_2$Ph(2-CF$_3$) | |
| A-28 | O | Me | H | H | Me | H | H | H | CN | CH$_2$Ph(3-CF$_3$) | |
| A-29 | O | Me | H | H | Me | H | H | H | CN | CH$_2$Ph(4-CF$_3$) | |

TABLE 1-continued

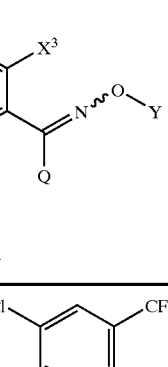

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-30 | O | Me | H | H | Me | H | H | H | CN | 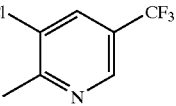 | 158–161 |
| A-31 | O | Me | H | H | Cl | H | H | H | CN | (same pyridine as above) | 162–165 |
| A-32 | O | Me | H | H | H | H | H | H | H | H | |
| A-33 | O | Me | H | H | H | H | H | H | H | Me | |
| A-34 | O | Me | H | H | H | H | H | H | H | Et | |
| A-35 | O | Me | H | H | H | H | H | H | H | Pr | |
| A-36 | O | Me | H | H | H | H | H | H | H | CH₂Ph | |
| A-37 | O | Me | H | H | H | H | H | H | Me | CH₂CH=CH₂ | 1.5421 |
| A-38 | O | Me | H | H | H | H | H | H | Me | CH₂Ph | 1.5742 |
| A-39 | O | Me | H | H | H | H | H | H | Me | Et | 1.5389 |
| A-40 | O | Me | H | H | H | H | H | H | Me | Me | 1.5475 |
| A-41 | O | Me | H | H | H | H | H | H | Ph | CH₂CH=CH₂ | 1.5869 | m.p.: Melting point
RI: Refractive index

TABLE 2

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-42 | O | Me | H | H | H | H | H | H | Ph | Me | 1.5939 |
| A-43 | O | Me | H | H | H | H | H | H | Ph | Et | 1.5795 |
| A-44 | O | Me | H | H | H | H | H | H | Ph(4-Cl) | Et | |
| A-45 | O | Me | H | H | Cl | H | H | H | Me | H | 124–127 |
| A-46 | O | Me | H | H | Cl | H | H | H | Me | Me | 69–72 |
| A-47 | O | Et | H | H | Cl | H | H | H | Me | Me | |
| A-48 | O | Pr | H | H | Cl | H | H | H | Me | Me | |
| A-49 | O | Me | H | H | Cl | H | H | H | Me | Et | 71–74 |
| A-50 | O | Me | H | H | Cl | H | H | H | Me | Pr | 1.5433 |
| A-51 | O | Me | H | H | Cl | H | H | H | Me | Pr-i | 1.6382 |
| A-52 | O | Me | H | H | Cl | H | H | H | Me | Bu | 38–40 |
| A-53 | O | Me | H | H | Cl | H | H | H | Me | Bu-s | 1.5332 |
| A-54 | O | Me | H | H | Cl | H | H | H | Me | Bu-i | 1.5338 |
| A-55 | O | Me | H | H | Cl | H | H | H | Me | Bu-t | 1.5269 |
| A-56 | O | Me | H | H | Cl | H | H | H | Me | CH₂Pr-c | 1.5531 |
| A-57 | O | Me | H | H | Cl | H | H | H | Me | Pen-c | |
| A-58 | O | Me | H | H | Cl | H | H | H | Me | CH₂CH=CH₃ | 69–72 |
| A-59 | O | Me | H | H | Cl | H | H | H | Me | CH₂C(Me)=CH₂ | |
| A-60 | O | Me | H | H | Cl | H | H | H | Me | CH₂CH=CHCO₂Et | |
| A-61 | O | Me | H | H | Cl | H | H | H | Me | CH₃CH≡CH | 85–88 |
| A-62 | O | Me | H | H | Cl | H | H | H | Me | CH₂CH₂CH₂Ph | 1.5597 |
| A-63 | O | Me | H | H | Cl | H | H | H | Me | CH₂COOEt | 1.5402 |
| A-64 | O | Me | H | H | Cl | H | H | H | Me | CH₂COOBu-t | 1.5211 |
| A-65 | O | Me | H | H | Cl | H | H | H | Me | CH₂CON(Me)₂ | |
| A-66 | O | Me | H | H | Cl | H | H | H | Me | CH₂CO₃H | |
| A-67 | O | Me | H | H | Cl | H | H | H | Me | CH₂OMe | 62–65 |
| A-68 | O | Me | H | H | Cl | H | H | H | Me | CH₂SMe | |
| A-69 | O | Me | H | H | Cl | H | H | H | Me | CH₂SOMe | |
| A-70 | O | Me | H | H | Cl | H | H | H | Me | CH₂CF₃ | 91–94 |
| A-71 | O | Me | H | H | Cl | H | H | H | Me | CH₂CN | 93–96 |
| A-72 | O | Me | H | H | Cl | H | H | H | Me | CH=CH₃ | |

TABLE 2-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-73 | O | Me | H | H | Cl | H | H | H | Me | Ph | 87–90 |
| A-74 | O | Me | H | H | Cl | H | H | H | Me | Ph(3-Cl) | |
| A-75 | O | Me | H | H | Cl | H | H | H | Me | Ph(4-Cl) | |
| A-76 | O | Me | H | H | Cl | H | H | H | Me | Ph(3-Me) | |
| A-77 | O | Me | H | H | Cl | H | H | H | Me | Ph(4-Me) | |
| A-78 | O | Me | H | H | Cl | H | H | H | Me | Ph(3-CF₃) | |
| A-79 | O | Me | H | H | Cl | H | H | H | Me | Ph(4-CF₃) | |
| A-80 | O | Me | H | H | Cl | H | H | H | Me | CH₂Ph | 65–68 |
| A-81 | O | Me | H | H | Cl | H | H | H | Me | CH₂Ph(2-F) | 80–82 |
| A-82 | O | Me | H | H | Cl | H | H | H | Me | CH₂Ph(3-F) | 88–91 |
| A-83 | O | Me | H | H | Cl | H | H | H | Me | CH₂Ph(4-F) | 101–103 |
| A-84 | O | Me | H | H | Cl | H | H | H | Me | CH₂Ph(2-Cl) | 88–91 |
| A-85 | O | Me | H | H | Cl | H | H | H | Me | CH₂Ph(3-Cl) | 68–71 |
| A-86 | O | Me | H | H | Cl | H | H | H | Me | CH₂Ph(4-Cl) | 103–106 |
| A-87 | O | Me | H | H | Cl | H | H | H | Me | CH₂Ph(2-Br) | 80–83 |
| A-88 | O | Me | H | H | Cl | H | H | H | Me | CH₂Ph(3-Br) | 79–81 |
| A-89 | O | Me | H | H | Cl | H | H | H | Me | CH₂Ph(4-Br) | 108–110 |
| A-90 | O | Me | H | H | Cl | H | H | H | Me | CH₂Ph(2-Me) | 88–91 |
| A-91 | O | Me | H | H | Cl | H | H | H | Me | CH₂Ph(3-Me) | 1.5722 |
| A-92 | O | Me | H | H | Cl | H | H | H | Me | CH₂Ph(4-Me) | 97–100 |
| A-93 | O | Me | H | H | Cl | H | H | H | Me | CH₂Ph(2-OMe) | 116–119 |
| A-94 | O | Me | H | H | Cl | H | H | H | Me | CH₂Ph(3-OMe) | 1.5789 |
| A-95 | O | Me | H | H | Cl | H | H | H | Me | CH₂Ph(4-OMe) | 1.5762 |
| A-96 | O | Me | H | H | Cl | H | H | H | Me | CH₂Ph(2-Bu-t) | |

TABLE 3

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-97 | O | Me | H | H | Cl | H | H | H | Me | CH₂Ph(3-Bu-t) | |
| A-98 | O | Me | H | H | Cl | H | H | H | Me | CH₂Ph(4-Bu-t) | 1.5552 |
| A-99 | O | Me | H | H | Cl | H | H | H | Me | CH₂Ph(2-CF₃) | 81–83 |
| A-100 | O | Me | H | H | Cl | H | H | H | Me | CH₂Ph(3-CF₃) | 1.5329 |
| A-101 | O | Me | H | H | Cl | H | H | H | Me | CH₂Ph(4-CF₃) | 117–118 |
| A-102 | O | Me | H | H | Cl | H | H | H | Me | CH₂Ph(3-CN) | 79–82 |
| A-103 | O | Me | H | H | Cl | H | H | H | Me | CH₂Ph(4-CN) | 121–124 |
| A-104 | O | Me | H | H | Cl | H | H | H | Me | CH₂Ph(4-NO₂) | |
| A-105 | O | Me | H | H | Cl | H | H | H | Me | CH₂Ph(4-COOMe) | 124–227 |
| A-106 | O | Me | H | H | Cl | H | H | H | Me | CH₂Ph(4-OCF₃) | 104–107 |
| A-107 | O | Me | H | H | Cl | H | H | H | Me | CH₂Ph(3-OPh) | |
| A-108 | O | Me | H | H | Cl | H | H | H | Me | CH₂Ph(4-OPh) | |
| A-109 | O | Me | H | H | Cl | H | H | H | Me | 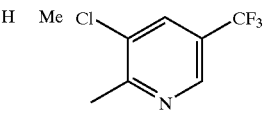 | 172–176 |
| A-110 | O | Me | H | H | Cl | H | H | H | Me | 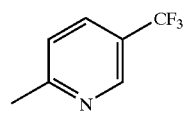 | |
| A-111 | O | Me | H | H | Cl | H | H | H | Et | Et | 79–82 |
| A-112 | O | Me | H | H | Me | H | H | H | H | CH₂Ph | 65–68 |
| A-113 | O | Me | H | H | Me | H | H | H | Me | CH₂Ph | 92–95 |
| A-114 | NH | Me | H | H | Me | H | H | H | H | CH₂Ph | |
| A-115 | NH | Me | H | H | Me | H | H | H | H | Me | |
| A-116 | NMe | Me | H | H | Me | H | H | H | H | Me | |
| A-117 | S | Me | H | H | Me | H | H | H | H | Pr | |
| A-118 | O | Me | H | H | Cl | Me | H | H | H | CH₂Ph | |
| A-119 | O | Me | Me | H | Cl | Me | H | H | H | Pr | |
| A-120 | O | Me | Me | H | Cl | Me | H | H | H | CH₂Ph | |
| A-121 | O | Me | CH₂OMe | H | Cl | Me | H | H | Me | Pr | |
| A-122 | O | Me | CH₂OMe | H | Cl | Me | H | H | Me | CH₂Ph | |
| A-123 | O | Me | CH₂CH=CH₂ | H | Cl | Me | H | H | Me | Pr | |
| A-124 | O | Me | CH₂CH=CH₂ | H | Cl | Me | H | H | Me | CH₂Ph | |
| A-125 | O | Me | CH₂C≡CH | H | Cl | H | H | H | Me | CH₂Ph | |
| A-126 | O | Me | CH₂C≡CH | H | Cl | H | H | H | Me | Et | |

TABLE 3-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-127 | O | Me | CH₂COMe | H | Cl | H | H | H | Me | CH₂Ph | |
| A-128 | O | Me | CH₂COMe | H | Cl | H | H | H | Me | Me | |
| A-129 | O | Me | CO₂Me | H | Cl | H | H | H | Me | CH₂Ph | |
| A-130 | O | Me | CO₂Me | H | Cl | H | H | H | Me | Ph | |
| A-131 | O | Me | COMe | H | CL | Me | H | H | Me | Pr | |
| A-132 | O | Me | COMe | H | Cl | Me | H | H | Me | CH₂Ph | |
| A-138 | O | Me | OMe | H | Cl | Me | H | H | Me | Pr | |
| A-134 | O | Me | OMe | H | Cl | Me | H | H | Me | CH₂Ph | |
| A-135 | O | Me | H | H | Cl | Me | H | H | Me | H | |
| A-136 | O | Me | H | H | Cl | Me | H | H | Me | Me | |
| A-137 | O | Me | H | H | Cl | Me | H | H | Me | Et | |
| A-138 | O | Me | H | H | Cl | Me | H | H | Me | Pr | |
| A-139 | O | Me | H | H | Cl | Me | H | H | Me | Pr-i | |
| A-140 | O | Me | H | H | Cl | Me | H | H | Me | Bu | |
| A-141 | O | Me | H | H | Cl | Me | H | H | Me | Bu-s | |
| A-142 | O | Me | H | H | Cl | Me | H | H | Me | Bu-i | |
| A-143 | O | Me | H | H | Cl | Me | H | H | Me | Bu-t | |
| A-144 | O | Me | H | H | Cl | Me | H | H | Me | CH₂CH=CH₂ | |
| A-145 | O | Me | H | H | Cl | Me | H | H | Me | CH₂C≡CH | |

TABLE 4

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-146 | O | Me | H | H | Cl | Me | H | H | Me | CH₂CN | |
| A-147 | O | Me | H | H | Cl | Me | H | H | Me | CH₂COOMe | |
| A-148 | O | Me | H | H | Cl | Me | H | H | Me | CH₂COOEt | |
| A-149 | O | Me | H | H | Cl | Me | H | H | Me | CH₂CO₂H | |
| A-150 | O | Me | H | H | Cl | Me | H | H | Me | CH₂Ph | 1.5821 |
| A-151 | O | Me | H | H | Cl | Me | H | H | Me | CH₂Ph(3-F) | 64–67 |
| A-152 | O | Me | H | H | Cl | Me | H | H | Me | CH₂Ph(4-F) | 85–88 |
| A-153 | O | Me | H | H | Cl | Me | H | H | Me | CH₂Ph(3-Cl) | 88–91 |
| A-154 | O | Me | H | H | Cl | Me | H | H | Me | CH₂Ph(4-Cl) | 107–110 |
| A-155 | O | Me | H | H | Cl | Me | H | H | Me | CH₂Ph(3-Me) | 1.5761 |
| A-156 | O | Me | H | H | Cl | Me | H | H | Me | CH₂Ph(4-Me) | 75–78 |
| A-157 | O | Me | H | H | Cl | Me | H | H | Me | CH₂Ph(3-OMe) | 73–76 |
| A-158 | O | Me | H | H | Cl | Me | H | H | Me | CH₂Ph(4-OMe) | 1.5788 |
| A-159 | O | Me | H | H | Cl | Me | H | H | Me | CH₂Ph(3-CF₃) | 88–89 |
| A-160 | O | Me | H | H | Cl | Me | H | H | Me | CH₂Ph(4-CF₃) | 100–103 |
| A-161 | O | Me | H | H | Me | H | Me | Me | Me | CH₂CO₂Me | |
| A-162 | O | Me | H | H | Me | Me | Me | Me | Me | CH₂C≡CH | |
| A-163 | O | Me | H | H | Cl | H | H | Cl | Me | CH₂CH=CH₂ | |
| A-164 | O | Me | H | H | Cl | H | H | Cl | Me | CH₂Ph | |
| A-165 | O | Me | H | H | OMe | H | H | H | Me | Et | |
| A-166 | O | Me | H | H | OMe | H | H | H | Me | Pr-i | |
| A-167 | O | Me | H | H | CF₃ | H | H | H | Me | Me | |
| A-168 | O | Me | H | H | CF₃ | H | H | H | Me | CH₂Ph | |
| A-169 | O | Me | H | H | OCF₃ | H | H | H | Me | Me | |
| A-170 | O | Me | H | H | OCF₃ | H | H | H | Me | CH₂Ph | |
| A-171 | O | Me | H | H | Cl | H | H | H | CF₃ | Me | |
| A-172 | O | Me | H | H | Cl | H | H | H | CF₃ | CH₂Ph | |
| A-173 | O | Me | H | H | Cl | H | H | H | Pr-c | CH₂CN | |
| A-174 | O | Me | H | H | Cl | H | H | H | Pr-c | CH₂OMe | |
| A-175 | O | Me | H | H | Cl | H | H | H | Me | CH₂OH | |
| A-176 | O | Me | H | H | Me | H | H | H | Me | CH₂OH | |
| A-177 | O | Me | H | H | Cl | H | H | H | Me | CH₂CH₂NH₂ | |
| A-178 | O | Me | H | H | Me | H | H | H | Me | CH₂CH₂NH₂ | |
| A-179 | O | Me | H | H | Cl | H | H | H | Me | CH₂CH₂N(Me)₂ | |
| A-180 | O | Me | H | H | Me | H | H | H | Me | CH₂CH₂N(Me)₂ | |
| A-181 | O | Me | H | H | Cl | H | H | H | Me | CH₃COMe | |
| A-182 | O | Me | H | H | Me | H | H | H | Me | CH₃COMe | |
| A-183 | O | Me | H | H | Cl | H | H | H | Me | CH₂CONHMe | |
| A-184 | O | Me | H | H | Me | H | H | H | Me | CH₂CONHMe | |
| A-185 | O | Me | H | H | Cl | H | H | H | Me | CH₂CH=CCl₂ | |
| A-186 | O | Me | H | H | Me | H | H | H | Me | CH₂CH=CCl₂ | |
| A-187 | O | Me | H | H | Cl | H | H | H | Me | CH₂(CH₂)₂CH=CH₂ | |
| A-188 | O | Me | H | H | Me | H | H | H | Me | CH₂(CH₂)₂CH=CH₂ | |
| A-189 | O | Me | H | H | Cl | H | H | H | Me | CH₂CH=CHMe | 1.5529 |
| A-190 | O | Me | H | H | Me | H | H | H | Me | CH₂CH=CHMe | |
| A-191 | O | Me | H | Me | Cl | H | H | H | Me | CH₂Ph | |

TABLE 4-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-192 | O | Me | H | Me | Cl | H | H | H | Me | Pr | |
| A-193 | O | Me | H | Me | Me | H | H | H | Me | CH₂Ph | |
| A-194 | O | Me | H | Me | Me | H | H | H | Me | Pr | |
| A-195 | O | Me | H | H | Cl | H | H | H | Me | CH₂C≡CCH₂CH₂OMe | |
| A-196 | O | Me | H | H | Cl | H | H | H | Me | CH₂C≡CCH₂OH | |
| A-197 | O | Me | H | H | Cl | H | H | H | Me | CH₂C≡CC(O)Me | |

TABLE 5

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-198 | O | Me | H | H | Cl | H | H | H | Me | CH₂CH₂CH=CH₂ | 1.5481 |
| A-199 | O | Me | H | H | H | H | H | H | Me | CH₂CH=CHCH₂OH | |
| A-200 | O | Me | H | H | H | H | H | H | Me | CH₂CH=CHCH₂OMe | |
| A-201 | O | Me | H | H | Cl | H | H | H | Me | CH₂CH=CHPh | 83–88 |
| A-202 | O | Me | H | H | H | H | H | H | Me | CH₂CH=CHPh(3-OMe,4-OH) | |
| A-203 | O | Me | H | H | H | H | H | H | Me | CH₂CH=CHPh(4-Cl) | |
| A-204 | O | Me | H | H | H | H | H | H | Me | CH₂CH=CHPh(2-Me) | |
| A-205 | O | Me | H | H | H | H | H | H | Me | CH₂CH=CHPh(3-NO₂) | |
| A-206 | O | Me | H | H | Cl | H | H | H | Me | CH₂Ph | 1.5769 |
| A-207 | O | Me | H | H | Cl | H | H | H | Me | CH₂Ph(2-Cl) | 1.5819 |
| A-208 | O | Me | H | H | Cl | H | H | H | Me | CH₂Ph(3-Cl) | 60–62 |
| A-209 | O | Me | H | H | Cl | H | H | H | Me | CH₂Ph(4-Cl) | 91–94 |
| A-210 | O | Me | H | H | H | H | Et | H | Me | CH₂Ph | |
| A-211 | O | Me | H | H | H | H | Pr-i | H | Me | CH₂Ph | |
| A-212 | O | Me | H | H | H | H | Hex | H | Me | CH₂Ph | |
| A-213 | O | Me | H | H | OEt | H | H | H | Me | CH₂Ph(4-Cl) | |
| A-214 | O | Me | H | H | OPr-i | H | H | H | Me | CH₂Ph(4-Cl) | |
| A-215 | O | Me | H | H | Cl | H | H | H | Me | 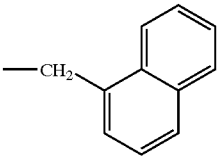 | 1.6189 |
| A-216 | O | Me | H | H | Cl | H | H | H | Me | CH(Me)Ph | 1.5745 |
| A-217 | O | Me | H | H | Cl | H | H | H | Me | CH₂Ph(2-OCF₃) | 72–74 |
| A-218 | O | Me | H | H | Cl | H | H | H | Me | CH₂Ph(3-OCF₃) | 73–74 |
| A-219 | O | Me | CH₂Ph(2-Cl) | H | Me | H | H | H | CN | CH₂Ph(2-Cl) | 1.5883 |
| A-220 | O | Me | H | H | Cl | H | H | H | Me | CH₂Ph(2-CN) | 89–92 |
| A-221 | O | Me | H | H | Br | H | H | H | Me | CH₂Ph(2-Cl) | |
| A-222 | O | Me | H | H | I | H | H | H | Me | CH₂Ph(2-Cl) | |
| A-223 | O | Me | H | H | H | H | Cl | H | Me | CH₂Ph(2-Cl) | |
| A-224 | O | Me | H | H | Cl | H | Cl | H | Me | CH₂Ph(2-Cl) | |
| A-225 | O | Me | H | H | Cl | H | H | H | Me | 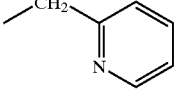 | 105–108 |
| A-226 | O | Me | H | H | Cl | H | H | H | Me | 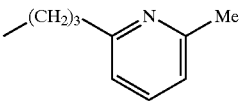 | |
| A-227 | O | Me | H | H | Cl | H | H | H | Me | 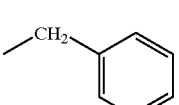 | 85–86 |
| A-228 | O | Me | H | H | Cl | H | H | H | Me | 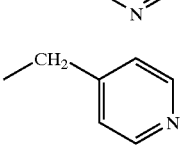 | 81–84 |

TABLE 5-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-229 | O | Me | H | H | Cl | H | H | H | Me | -CH₂-CH₂-N(morpholine) | 1.5532 |
| A-230 | O | Me | H | H | Cl | H | H | H | Me | CH₂C≡CPen-c | |
| A-231 | O | Me | H | H | Cl | H | H | H | Me | 2-(COMe)cyclopentyl | |
| A-232 | O | Me | H | H | Cl | H | H | H | Me | 2-(OH)cyclopentyl | |

TABLE 6

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-233 | O | Me | H | H | Cl | H | H | H | Me | 1-(Me)cyclopentyl | |
| A-234 | O | Me | H | H | Cl | H | H | H | Me | CH₂CH₂N(Me)₂ | 1.5461 |
| A-235 | O | Me | H | H | Cl | H | H | H | Me | 2-Me-pyrimidin-?-yl | 128–130 |
| A-236 | O | Me | H | H | Cl | H | H | H | Me | 4-Cl-2-SMe-6-Me-pyrimidinyl | |
| A-237 | O | Me | H | H | Cl | H | H | H | Me | 4,6-(OMe)₂-2-Me-pyrimidinyl | 130–131 |
| A-238 | O | Me | H | H | Cl | H | H | H | Me | 2,4,6-tri-Me-pyrimidinyl | |
| A-239 | O | Me | H | H | Cl | H | H | H | Me | 2-Cl-4-Me-pyrimidinyl | |

TABLE 6-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-240 | O | Me | H | H | Cl | H | H | H | Me | CH₂-oxiranyl | 1.5581 |
| A-241 | O | Me | H | H | Cl | H | H | H | Me | CH₂-(1,3-dioxolan-2-yl) | 1.5541 |
| A-242 | O | Me | H | H | Cl | H | H | H | Me | CH₂Hex-c | 86–87 |
| A-243 | O | Me | H | H | Cl | H | H | H | Me | 2-methoxycyclohexyl | |
| A-244 | O | Me | H | H | Cl | H | H | H | Me | 4-methylcyclohexyl | |
| A-245 | O | Me | H | H | Cl | H | H | H | Me | 4,6-dimethoxy-1,3,5-triazin-2-yl (via OCH₂, CH₂O) | 144–146 |
| A-246 | O | Me | H | H | Cl | H | H | H | Me | 4-chloro-6-methoxy-1,3,5-triazin-2-yl | |
| A-247 | O | Me | H | H | Cl | H | H | H | Me | quinolin-2-yl | |
| A-248 | O | Me | H | H | Cl | H | H | H | Me | CH₂-(naphthalen-2-yl) | 88–91 |
| A-249 | O | Me | H | H | Cl | H | H | H | Me | CH₂-(benzothiazol-2-yl) | |

TABLE 7

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-250 | O | Me | H | H | H | H | H | H | Me | 2-isopropyl-6-fluoro-5-hydroxybenzothiazol-yl | |
| A-251 | O | Me | H | H | Cl | H | H | H | Me | —(CH₂)₆Me | 1.5272 |

TABLE 7-continued

| Comp. No. | G | $R^1$ | $R^2$ | $R^3$ | $X^1$ | $X^2$ | $X^3$ | $X^4$ | Q | Y | m.p.(° C.) or RI($n_D^{20}$) |
|---|---|---|---|---|---|---|---|---|---|---|---|
| A-252 | O | Me | H | H | Cl | H | H | H | Me | $CH_2Ph(2,3-(Cl)_2)$ | 103–106 |
| A-253 | O | Me | H | H | Cl | H | H | H | Me | $CH_2Ph(2,4-(Cl)_2)$ | 119–120 |
| A-254 | O | Me | H | H | Cl | H | H | H | Me | $CH_2Ph(2,5-(Cl)_2)$ | 96–99 |
| A-255 | O | Me | H | H | Cl | H | H | H | Me | $CH_2Ph(2,5-(Cl)_2)$ | 140–143 |
| A-256 | O | Me | H | H | Cl | H | H | H | Me | $CH_2Ph(3,4-(Cl)_2)$ | 94–96 |
| A-257 | O | Me | H | H | Cl | H | H | H | Me | $CH_2Ph(3,5-(Cl)_2)$ | 96–98 |
| A-258 | O | Me | H | H | Cl | H | H | H | Me | $CH_2Ph(2,5-(Me)_2)$ | 88–91 |
| A-259 | O | Pr-i | H | H | H | H | H | H | Me | $CH_2Ph(2-Cl)$ | |
| A-260 | O | Me | H | Pr-i | Cl | H | H | H | Me | $CH_2Ph(2-Cl)$ | |
| A-261 | O | Me | H | H | Cl | H | H | H | Me | 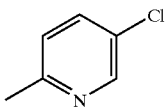 | 168–171 |
| A-262 | O | Me | H | H | Cl | H | H | H | Me | 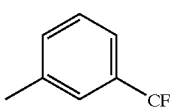 | |
| A-263 | O | Me | H | H | Cl | H | H | H | Me | 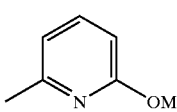 | |
| A-264 | O | Me | H | H | Cl | H | H | H | Me | 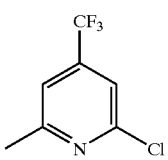 | |
| A-265 | O | Me | H | H | Cl | H | H | H | Me | 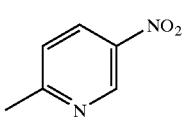 | |
| A-266 | O | Me | H | H | Cl | H | H | H | Me | $CH_2Ph(3-NO_2)$ | 1.5811 |
| A-267 | O | Me | H | H | Cl | H | H | H | Me | $CH_2Ph(4-COMe)$ | 121–124 |
| A-268 | O | Me | H | H | $CH_2Br$ | H | H | H | Me | $CH_2Ph(2-CH_2)$ | |
| A-269 | O | Me | H | H | Cl | H | H | H | Me | $CH_2Ph(8-COMe)$ | 1.5829 |
| A-270 | O | Me | H | H | H | H | $CH_2Cl$ | H | Me | $CH_2Ph(2-CH_2)$ | |
| A-271 | O | Me | H | H | $OCH_2Cl$ | H | H | H | Me | $CH_2Ph(4-CH_2)$ | |
| A-272 | O | Me | H | H | Cl | H | H | H | Me | 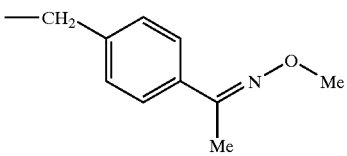 | 105–108 |
| A-273 | O | Me | H | H | Cl | H | H | H | H | Pr-i | 1.5881 |
| A-274 | O | Me | H | H | Cl | H | H | H | Hex-c | $CH_2Ph$ | |
| A-275 | O | Me | H | H | H | H | H | H | SMe | $CH_2Ph$ | |
| A-276 | O | Me | H | H | H | H | H | H | S(O)Me | $CH_2Ph$ | |
| A-277 | O | Me | H | H | Cl | H | H | H | CN | $CH_2CH_2Ph$ | 87–90 |
| A-278 | O | Me | H | H | Cl | H | H | H | Me | $CH_2Ph(3-CO_2Me)$ | 70–73 |
| A-279 | O | Me | H | H | Cl | H | H | H | Me | $CH_2Ph(3,5-(Me)_2)$ | 79–82 |
| A-280 | O | Me | H | H | H | H | H | H | Me | $CH_2CH_2NO_2$ | |
| A-281 | O | Me | H | H | Cl | H | H | H | Me | $CH_2CH_2NHEt$ | |
| A-282 | O | Me | H | H | Cl | H | H | H | Me | 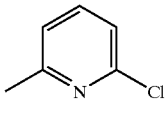 | 153–156 |

TABLE 7-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-283 | O | Me | H | H | Cl | H | H | H | Me | 3-Cl-2-methylpyridin-yl | 122–125 |

TABLE 8

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-284 | O | Me | H | H | Cl | H | H | H | Me | 3-chloro-6-methylpyridazin-yl | |
| A-285 | O | Me | H | H | Cl | H | H | H | Me | —CH₂-(6-chloropyridin-2-yl) | 76–78 |
| A-286 | O | Me | H | H | Cl | H | H | H | Me | —CH₂-(6-methylpyridin-2-yl) | 93–96 |
| A-287 | O | Me | H | H | Cl | H | H | H | CN | —CH₂-(pyridin-2-yl) | 103–106 |
| A-288 | O | Me | H | H | Cl | H | H | H | Et | —CH₂-(6-methylpyridin-2-yl) | 1.5659 |
| A-289 | O | Me | H | H | Cl | H | H | H | SO₂Me | CH₂Ph(2-Cl) | 1.5713 |
| A-290 | O | Me | H | H | Cl | H | H | H | SO₂Me | —CH₂-(pyridin-2-yl) | 1.5681 |
| A-291 | O | Me | H | H | Cl | H | H | H | Me | CH₂Ph(3-C(Me)=NOMe) | 1.5869 |
| A-292 | O | Me | H | H | Cl | H | H | H | Et | CH₂COMe | 1.5421 |
| A-293 | O | Me | H | H | Cl | H | H | H | Et | CH₂C(Me)=NOMe | 1.5262 |
| A-294 | O | Me | H | H | Me | H | H | H | Me | CH₂Ph(2-Cl) | 103–106 |
| A-295 | O | Me | H | H | Me | H | H | H | Me | CH₂Ph(2-Me) | 95–98 |
| A-296 | O | Me | H | H | Cl | H | H | H | Et | CH₂Ph(2-Cl) | 74–77 |
| A-297 | O | Me | H | H | Cl | H | H | H | Et | CH₂Ph(2-CF₃) | 1.5238 |
| A-298 | O | Me | H | H | Cl | H | H | H | Et | CH(Me)COMe | 1.5258 |
| A-299 | O | Me | H | H | Cl | H | H | H | Et | CH(Me)C(Me)=NOMe | 1.5241 |
| A-300 | O | Me | H | H | Cl | H | H | H | Et | CH(Me)C(Me)=NOEt | 1.5218 |
| A-301 | O | Me | H | H | Cl | H | H | H | Me | CH₂C≡CCH₂NH₂ | |
| A-302 | O | Me | H | H | Cl | H | H | H | Me | CH₂C≡CCO₂Me | |
| A-303 | O | Me | H | H | Cl | H | H | H | Et | CH₂Ph | 1.5757 |
| A-304 | O | Me | H | H | Cl | H | H | H | Et | CH₂Ph(3-OMe) | 1.5649 |
| A-305 | O | Me | H | H | Cl | H | H | H | Et | —CH₂-(pyridin-2-yl) | 1.5691 |

TABLE 8-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-306 | O | Me | H | H | Cl | H | H | H | Me | 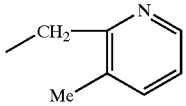 | 121–124 |
| A-307 | O | Me | H | H | Cl | H | H | H | Me | 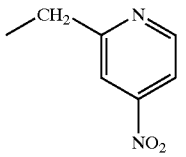 | |
| A-308 | O | Me | H | H | Cl | H | H | H | Me | 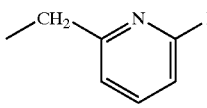 | |
| A-309 | O | Me | H | H | Cl | H | H | H | Me | CH(Me)Ph(2-Cl) | 1.5749 |
| A-310 | O | Me | H | H | Cl | H | H | H | Me | CH(Me)Ph(3-Cl) | 1.5792 |
| A-311 | O | Me | H | H | Cl | H | H | H | Me | CH(Me)Ph(4-Cl) | 99–102 |
| A-312 | O | Me | H | H | Cl | H | H | H | Me | CH(Me)Ph(3-OMe) | 1.5734 |
| A-313 | O | Me | H | H | Cl | H | H | H | Me | CH(Me)Ph(3-CF₃) | 1.5369 |
| A-314 | O | Me | H | H | Me | H | H | H | Me | CH₂Ph(2-CF₃) | 107–110 |
| A-315 | O | Me | H | H | Me | H | H | H | Me | CH₂Ph(3-OMe) | 1.5621 |
| A-316 | O | Me | H | H | H | H | H | H | Me | Ph(3,5-Cl₂) | |
| A-317 | O | Me | H | H | H | H | H | H | Me | Ph(2-NO₂) | |
| A-318 | O | Me | H | H | H | H | H | H | Me | Ph(3-Br) | |

TABLE 9

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-319 | O | Me | H | H | H | H | H | H | Me | Ph(4-F) | |
| A-320 | O | Me | H | H | Cl | Cl | H | H | Me | CH₂Ph(2-Me) | 89–92 |
| A-321 | O | Me | H | H | Cl | Cl | H | H | Me | CH₂Ph(2-Cl) | 118–121 |
| A-322 | O | Me | CH₂Ph(3-OMe) | H | Me | H | H | H | Me | CH₂Ph(3-OMe) | 1.5653 |
| A-323 | O | Me | H | H | F | H | H | H | Me | CH₂Ph | 59–62 |
| A-324 | O | Me | H | H | F | H | H | H | Me | CH₂Ph(2-F) | 63–64 |
| A-325 | O | Me | H | H | F | H | H | H | Me | CH₂Ph(2-Cl) | 66–67 |
| A-326 | O | Me | H | H | F | H | H | H | Me | CH₂Ph(2-Br) | 56–57 |
| A-327 | O | Me | H | H | F | H | H | H | Me | CH₂Ph(2-Me) | 80–81 |
| A-328 | O | Me | H | H | F | H | H | H | Me | CH₂Ph(2-CF₃) | 73–74 |
| A-329 | O | Me | H | H | F | H | H | H | Me | CH₂Ph(3-OMe) | 1.5651 |
| A-330 | O | Me | H | H | F | H | H | H | Me | 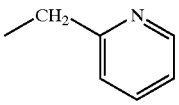 | 81–83 |
| A-331 | O | Me | H | H | Cl | Me | H | H | Me | CH₂Ph(2-Cl) | 103–104 |
| A-332 | O | Me | H | H | Cl | Cl | H | H | Me | 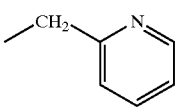 | 1.5823 |
| A-333 | O | Me | H | H | Me | H | H | H | Me | 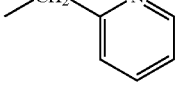 | 1.5641 |

TABLE 9-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-334 | O | Me | H | H | Cl | H | H | H | Me | (CH₂-pyridine with 5-Me) | 82–85 |
| A-335 | O | Me | H | H | Cl | H | H | H | Me | (CH₂-pyridine with 2-SMe) | |
| A-336 | O | Me | H | H | Cl | H | H | H | Me | (CH₂-pyridine with 2-CO₂Me) | |
| A-337 | O | Me | H | H | H | H | H | H | Me | (CH₂-pyridine with 2-C(O)NMe) | |
| A-338 | O | Me | H | H | H | H | H | H | Me | CH₂Ph(2-Cl) | 1.5711 |
| A-339 | O | Me | H | H | H | H | H | H | Me | CH₂Ph(3-Cl) | 1.5788 |
| A-340 | O | Me | H | H | H | H | H | H | Me | CH₂Ph(4-Cl) | 72–75 |
| A-341 | O | Me | H | H | Cl | H | H | H | Pr-c | CH₂Ph(2-Cl) | 1.5781 |
| A-342 | O | Me | H | H | Me | H | H | H | Me | CH₂Ph(2-F) | 93–96 |
| A-343 | O | Me | H | H | H | H | H | H | Me | CH₂Ph(2-Me) | 1.5739 |
| A-344 | O | Me | H | H | H | H | H | H | Me | CH₂Ph(3-Me) | 1.5729 |
| A-345 | O | Me | H | H | H | H | H | H | Me | CH₂Ph(4-Me) | 75–78 |
| A-346 | O | Me | H | H | Cl | Me | H | H | Me | CH₂Ph(2-Me) | 82–85 |
| A-347 | O | Me | H | H | Cl | Me | H | H | Me | CH₂Ph(2-CF₃) | 71–73 |
| A-348 | O | Me | H | H | H | H | H | H | Me | CH₂Ph(2-CF₃) | 1.5399 |
| A-349 | O | Me | H | H | H | H | H | H | Me | CH₂Ph(3-CF₃) | 1.5349 |
| A-350 | O | Me | H | H | H | H | H | H | Me | CH₂Ph(4-CF₃) | 1.5291 |
| A-351 | O | Me | H | H | H | H | H | H | Me | Ph(3-CO₂Me) | |
| A-352 | O | Me | H | H | R | H | H | H | Me | Ph(2-NO₂,4-Cl) | |
| A-353 | O | Me | H | H | H | H | H | H | Me | Ph(3-Cl,5-OMe) | |
| A-354 | O | Me | H | H | Cl | Me | H | H | Me | CH₂Ph(2-OMe) | 89–92 |
| A-355 | O | Me | H | H | Cl | Me | H | H | Me | (CH₂-2-pyridyl) | 73–76 |

TABLE 10

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-356 | O | Me | H | H | Cl | Me | H | H | Me | CH₂Ph(2-CN) | 107–110 |
| A-357 | O | Me | H | H | Cl | Me | H | H | Me | CH₂Ph(3-CN) | 95–98 |
| A-358 | O | Me | H | H | Me | Me | H | H | Me | CH₂Ph(2-Cl) | 107–110 |
| A-359 | O | Me | H | H | Cl | H | H | H | Pr-c | CH₂Ph(2-Me) | 94–97 |
| A-360 | O | Me | H | H | Me | H | H | H | Me | CH₂Ph(2-CN) | 63–66 |
| A-361 | O | Me | CH₂Ph(2-CN) | H | Me | H | H | H | Me | CH₂Ph(2-CN) | 1.5761 |
| A-362 | O | Me | H | H | Me | H | H | H | Me | CH₂Ph(3-Me) | 69–72 |
| A-363 | O | Me | H | H | Me | H | H | H | Me | CH₂Ph(4-Me) | 92–95 |
| A-364 | O | Me | H | H | Me | H | H | H | Me | CH₂Ph(3-Cl) | 68–70 |
| A-365 | O | Me | H | H | Me | H | H | H | Me | CH₂Ph(4-Cl) | 86–89 |
| A-366 | O | Me | CH₂Ph(4-Cl) | H | Me | H | H | H | Me | CH₂Ph(4-Cl) | 1.5778 |
| A-367 | O | Me | H | H | Cl | Me | H | H | Me | CH₂Ph(2-F) | 85–88 |
| A-368 | O | Me | H | H | Me | H | H | H | Me | CH₂C(Me)=NOMe | 1.5362 |

TABLE 10-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-369 | O | Me | H | H | Me | H | H | H | Me | CH₂CH₂Ph | 1.5661 |
| A-370 | O | Me | H | H | Cl | H | H | H | Me | 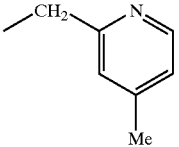 | 76–81 |
| A-371 | O | Me | H | H | F | H | H | H | Me | CH₂Ph(3-Cl) | 48–51 |
| A-372 | O | Me | H | H | F | H | H | H | Me | CH₂Ph(4-Cl) | 85–88 |
| A-373 | O | Me | H | H | F | H | H | H | Me | CH₂Ph(3-Me) | 1.5601 |
| A-374 | O | Me | H | H | F | H | H | H | Me | CH₂Ph(4-Me) | 84–87 |
| A-375 | O | Me | H | H | F | H | H | H | Me | CH₂Ph(3-CF₃) | 50–52 |
| A-376 | O | Me | H | H | F | H | H | H | Me | CH₂Ph(4-CF₃) | 79–82 |
| A-377 | O | Me | H | H | F | H | H | H | Me | CH₂Ph(2-CN) | 87–90 |
| A-378 | O | Me | H | H | F | H | H | H | Me | CH(Me)Ph(2-Cl) | 1.5621 |
| A-379 | O | Me | H | H | F | H | H | H | Me | CH(Me)Ph(3-Cl) | 1.5599 |
| A-380 | O | Me | H | H | F | H | H | H | Me | CH(Me)Ph(4-Cl) | 85–88 |
| A-381 | O | Me | H | H | Me | Me | Me | Me | Me | CH₂Ph | |
| A-382 | O | Me | H | H | Cl | Cl | Cl | Cl | Me | CH₂Ph | |
| A-383 | O | Me | H | H | Cl | H | H | H | Pr-c | CH₂Ph | 1.5731 |
| A-384 | O | Me | H | H | Cl | Me | H | H | Me | CH₂Ph(4-CN) | 120–122 |
| A-385 | O | Me | H | H | H | H | H | H | Me | Ph(2-CN,3-Cl) | |
| A-386 | O | Me | H | H | H | H | H | H | Me | CH₂Ph(2,3-(Cl)₂) | 71–74 |
| A-387 | O | Me | H | H | H | H | H | H | Me | CH₂Ph(2,4-(Cl)₂) | 96–99 |
| A-388 | O | Me | H | H | H | H | H | H | Me | CH₂Ph(2,5-(Cl)₂) | 94–97 |
| A-389 | O | Me | H | H | H | H | H | H | Me | CH₂Ph(2,6-(Cl)₂) | 92–95 |
| A-390 | O | Me | H | H | H | H | H | H | Me | CH₂Ph(3,4-(Cl)₂) | 56–59 |
| A-391 | O | Me | H | H | H | H | H | H | Me | CH₂Ph(3,5-(Cl)₂) | 76–78 |
| A-392 | O | Me | H | H | H | H | H | H | Me | Ph(3,4,6-Cl₂) | |
| A-393 | O | Me | H | H | H | H | H | H | Me | Ph(3-Cl,5-OH) | |
| A-394 | O | Me | H | H | Cl | H | H | H | Me | CH₂COPh | 1.5768 |
| A-395 | O | Me | H | H | Cl | H | H | H | Me | 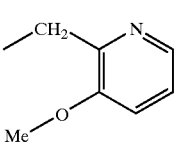 | 147–150 |
| A-396 | O | Me | H | H | Cl | H | H | H | Me | 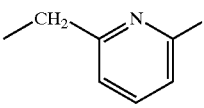 | |
| A-397 | O | Me | H | H | Cl | H | H | H | Me | 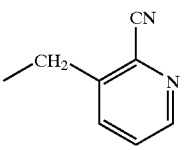 | |

TABLE 11

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-398 | O | Me | H | H | H | H | H | H | Me | CH₂Ph(2-F) | 1.5657 |
| A-399 | O | Me | H | H | H | H | H | H | Me | CH₂Ph(3-F) | 1.5641 |
| A-400 | O | Me | H | H | H | H | H | H | Me | CH₂Ph(4-F) | 88–91 |
| A-401 | O | Me | H | H | Cl | H | H | H | Me | CH₂COPh(4-Me) | 90–93 |
| A-402 | O | Me | H | H | Cl | H | H | H | Me | 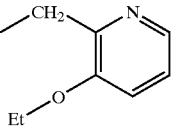 | 99–102 |

TABLE 11-continued

| Comp. No. | G | R¹ | R² | R³ | X¹ | X² | X³ | X⁴ | Q | Y | m.p.(° C.) or RI(n_D²⁰) |
|---|---|---|---|---|---|---|---|---|---|---|---|
| A-403 | O | Me | H | H | Cl | H | H | H | Me | CH₂COPh(4-Cl) | 99–102 |
| A-404 | O | Me | H | H | Cl | H | H | H | Me | CH₂COPh(4-OMe) | 63–66 |
| A-405 | O | Me | H | H | Cl | H | H | H | Pr-c | 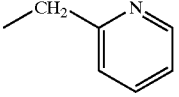 | 1.5687 |
| A-406 | O | Me | H | H | Cl | H | H | H | Me | CH(Me)Ph(2-Me) | 1.5719 |
| A-407 | O | Me | H | H | Cl | H | H | H | Me | CH(Me)Ph(3-Me) | 1.5702 |
| A-408 | O | Me | H | H | Cl | H | H | H | Me | CH(Me)Ph(4-Me) | 1.5693 |
| A-409 | O | Me | H | H | Cl | H | H | H | Me | 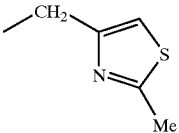 | 98–101 |
| A-410 | O | Me | H | H | Cl | H | H | H | Me | 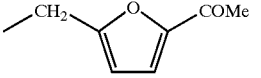 | |
| A-411 | O | Me | H | H | Cl | H | H | H | Me | 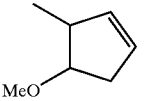 | |
| A-412 | O | Me | H | H | Cl | H | H | H | Me | CH(C(Me)=NOMe)₂ | 1.5411 |
| A-413 | O | Me | H | H | Cl | H | H | H | Me | 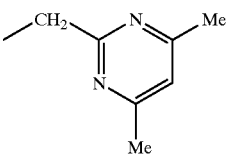 | 123–126 |
| A-414 | O | Me | H | H | Cl | H | H | H | Me | CH₂Ph(2-NO₂) | 104–107 |
| A-415 | O | Me | H | H | Cl | H | H | H | Me | 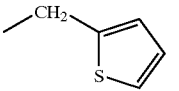 | 74–77 |
| A-416 | O | Me | H | H | Cl | H | H | H | Me | 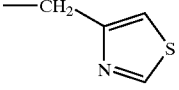 | 76–79 |
| A-417 | O | Me | H | H | Cl | H | H | H | Me | 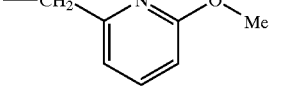 | 93–95 |
| A-418 | O | Me | H | H | Cl | H | H | H | Me | 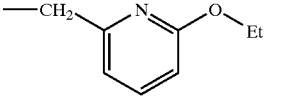 | 56–59 |
| A-419 | O | Me | H | H | Cl | H | H | H | Me | 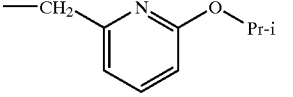 | 68–71 |

TABLE 11-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-420 | O | Me | H | H | H | H | H | H | Me | —CH₂-(6-methyl-pyridin-2-yl) | 1.5731 |
| A-421 | O | Me | H | H | Cl | H | H | H | Me | 2-benzothiazolyl | 116–119 |

TABLE 12

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-422 | O | Me | H | H | Cl | H | H | H | Me | —CH₂-(2-CF₃-thiazol-4-yl) | 83–86 |
| A-423 | O | Me | H | H | Cl | H | H | H | Me | —CH₂-(3-methoxy-6-methyl-pyridin-2-yl) | 103–105 |
| A-424 | O | Me | H | H | Cl | H | H | H | Me | 4-methyl-4-hydroxycyclohex-2-enyl | |
| A-425 | O | Me | H | H | Cl | H | H | H | Me | 2-methyl-3-methyl-5-isopropylcyclohexyl | |
| A-426 | O | Me | H | H | Cl | H | H | H | Me | —CH₂-(4-methyl-thiazol-2-yl) | 64–67 |
| A-427 | O | Me | H | H | F | H | H | H | Me | CH₂Ph(3-OCF₃) | 35–37 |
| A-428 | O | Me | H | H | F | H | H | H | Me | CH₂Ph(3-CN) | 1.5666 |
| A-429 | O | Me | H | H | Cl | Me | H | H | Me | —CH₂-(6-methyl-pyridin-2-yl) | 1.5769 |
| A-430 | O | Me | H | H | F | H | H | H | Me | —CH₂-(6-methyl-pyridin-2-yl) | 1.5609 |
| A-431 | O | Me | H | H | Cl | H | H | H | Me | —CH₂-(quinolin-2-yl) | 97–100 |

TABLE 12-continued

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-432 | O | Me | H | H | Cl | H | H | H | Me | —CH₂— 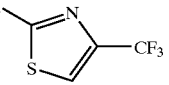 | 93–96 |
| A-433 | O | Me | H | H | Cl | H | H | H | Me | —CH₂— 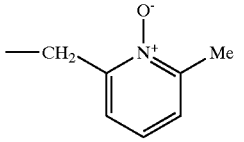 | 141–144 |
| A-434 | O | Me | H | H | Me | H | H | H | Me | —CH₂— 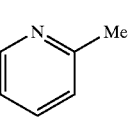 | 72–75 |
| A-435 | O | Me | Me | H | Cl | Me | H | H | Me | CH₂Ph(2-Cl) | 1.5714 |
| A-436 | O | Me | H | H | Cl | H | H | H | H | CH₂Ph(2-Cl) | 89–91 |
| A-437 | O | Me | H | H | Cl | H | H | H | H | CH₂Ph(3-Cl) | 90–93 |
| A-438 | O | Me | H | H | Cl | H | H | H | H | CH₂Ph(4-Cl) | 137–140 |
| A-439 | O | Me | H | H | Cl | H | H | H | H | —CH₂— 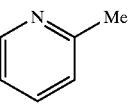 | 1.5839 |
| A-440 | O | Me | H | H | F | H | H | H | Me | —CH₂— 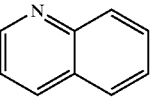 | 1.6004 |
| A-441 | O | Me | H | H | Cl | Me | H | H | Me | —CH₂— 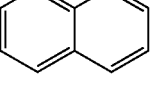 | 111–114 |
| A-442 | O | Me | H | H | Cl | Me | H | H | Me | CH₂Ph(2-Cl) | 88–91 |

TABLE 13

| Comp. No. | G | R¹ | R² | R³ | X¹ | X² | X³ | X⁴ | Q | Y | m.p.(° C.) or RI($n_D^{20}$) |
|---|---|---|---|---|---|---|---|---|---|---|---|
| A-443 | O | Me | H | H | Cl | H | H | H | Me | —CH₂—  | 1.5549 |
| A-444 | O | Me | H | H | Cl | H | H | H | Me | 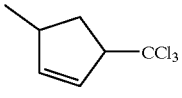 | |
| A-445 | O | Me | H | H | Cl | H | H | H | Me | —CH₂— 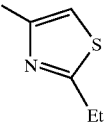 | 1.5825 |

TABLE 13-continued

| Comp. No. | G | $R^1$ | $R^2$ | $R^3$ | $X^1$ | $X^2$ | $X^3$ | $X^4$ | Q | Y | m.p.(° C.) or $RI(n_D^{20})$ |
|---|---|---|---|---|---|---|---|---|---|---|---|
| A-446 | O | Me | H | H | Cl | H | H | H | Me |  | |
| A-447 | O | Me | H | H | Cl | H | H | H | Me |  | 1.5689 |
| A-448 | O | Me | H | H | Cl | H | H | H | Me |  | 94–97 |
| A-449 | O | Me | H | H | Cl | H | H | H | Me |  | 111–114 |
| A-450 | O | Me | H | H | Cl | H | H | H | Me |  | 1.5649 |

Typical processes for producing the carbamate derivative represented by the general formula [I] as the compound of the present invention, will be exemplified below. Here, the novel compound represented by the general formula [I] has a C=N double bond and thereby may form as an E/Z isomer mixture in some cases. The isomer mixture can be isolated into individual component by a purification method such as crystallization or column chromatography. An individual isomer and a mixture thereof are included in the present invention.

Production process 1

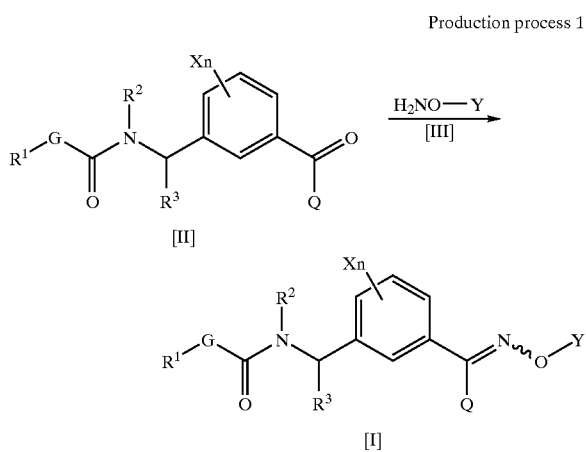

(wherein each of G, $R^1$, $R^2$, $R^3$, Q, X, Y and n is as defined above.)

The compound [I] of the present invention can be produced by reacting a compound [II] and a compound [III] in an inert solvent (see Jikken kagaku Kouza (Experimental Chemical Lecture), fourth edition, vol. 20, p. 349–355 (The Chemical Society of Japan) for example). Here, the material compound [III] to be used in the present production process may form a salt with e.g. hydrochloric acid or sulfuric acid. The compound [III] may be produced in accordance with a known process (see Jikken kagaku Kouza, fourth edition, vol. 20, p. 342–349 for example).

With respect to the amount of the material compound to be used in the present reaction, the compound [III] is properly selected within a range of from 1 to 50 equivalents based on the compound [II], preferably from 1 to 10 equivalents. The inert solvent which can be used in the present production process may, for example, be an alcohol such as methanol, ethanol, propanol or isopropanol, an ether such as diethyl ether, diisopropyl ether, tetrahydrofuran, dioxane, dimethoxyethane or diethylene glycol dimethyl ether, an aromatic hydrocarbon such as benzene, chlorobenzene, nitrobenzene or toluene, or water. These inert solvents may be used alone or as mixed.

In the present production process, an acid such as hydrochloric acid or acetic acid, or a base such as sodium acetate, sodium carbonate or sodium hydrogencarbonate, may coexist, and they may be used alone or in combination. The amount is properly selected within a range of from 0.001 to 50 equivalents based on the compound [II], preferably from 0.01 to 10 equivalents. The reaction temperature is within a range of from −10° C. to the boiling point of the inert solvent to be used, and preferably within a range of from 0° C. to the boiling point of the inert solvent to be used. The reaction time varies depending upon e.g. the reaction temperature and the reaction amount, but may be selected within a range of from 1 to 48 hours in general. After completion of the reaction, the desired product is isolated from the reaction system by a conventional method and may be purified by Production process 2

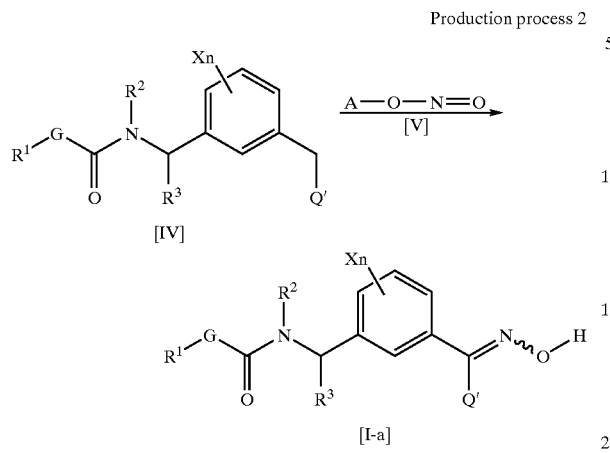

[IV]

[I-a]

(wherein each of G, $R^1$, $R^2$, $R^3$, X and n is as defined above, Q' is a cyano group or a nitro group, and A is a $C_1$–$C_{10}$ alkyl group.)

A compound [I-a] of the present invention can be produced by reacting a compound [IV] and a nitrite ester [V] in the presence of a base (see Organic Syntheses, vol. 6, p.199 (1988) for example). With respect to the amount of the material compound to be used in the present reaction, the compound [V] is properly selected within a range of from 1 to 50 equivalents based on the compound [IV], preferably from 1 to 10 equivalents.

The base to be used in the present production process may, for example, be an alkali metal alcoholate such as sodium methoxide, sodium ethoxide or potassium tert-butoxide, or an inorganic base such as sodium hydroxide, potassium hydroxide, sodium carbonate or potassium carbonate, and the amount of the base is properly selected within a range of from 0.5 to 50 equivalents based on the compound [IV], preferably from 1 to 10 equivalents.

The inert solvent which can be used in the present production process may be one which does not inhibit the progress of the present production process, and an ether such as diethyl ether, diisopropyl ether, tetrahydrofuran, dioxane, 1,2-dimethoxyethane or diethylene glycol dimethyl ether, a halogenated hydrocarbon such as dichloromethane, chloroform, carbon tetrachloride or tetrachloroethane, an aromatic hydrocarbon such as benzene, chlorobenzene or toluene, or an alcohol such as methanol, ethanol, propanol or isopropanol, may, for example, be used. These inert solvents may be used alone or as mixed.

The reaction temperature is within a range of from −70° C. to the boiling point of the inert solvent to be used, and preferably from −20° C. to the boiling point of the inert solvent to be used. The reaction time varies depending upon e.g. the reaction temperature and the reaction amount, but may be selected within a range of from 1 to 100 hours in general, preferably from 12 to 75 hours.

After completion of the reaction, the desired product is isolated from reaction system by a conventional method and may be purified by e.g. column chromatography or recrystallization, as the case requires.

Production process 3

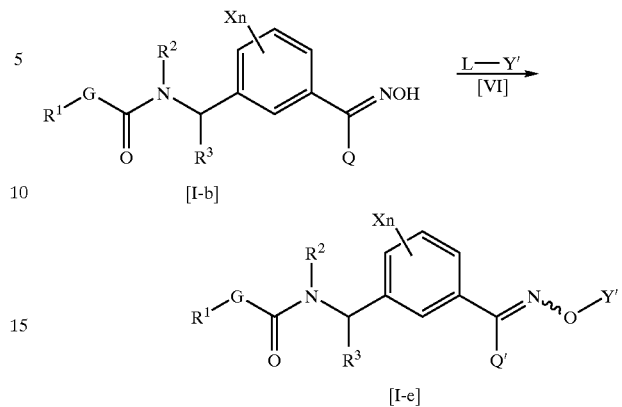

[I-b]

[I-e]

(wherein each of G, $R^1$, $R^2$, $R^3$, X, Q and n is as defined above, Y' has the same meaning as the above-mentioned Y except for hydrogen, and L is a leaving group and is a halogen atom or a sulfonate such as tosyloxy or mesyloxy.)

A compound [I-e] of the present invention can be produced by reacting a compound [I-b] of the present invention and a compound [VI] in the presence of a base.

With respect to the amount of the material compound to be used in the present reaction, the compound [VI] is properly selected within a range of from 1 to 50 equivalents based on the compound [I-b], preferably from 1 to 5 equivalents.

An inert solvent may be used in the present production process in some cases. The inert solvent may be one which does not inhibit the progress of the present reaction, and a ketone such as acetone, methyl ethyl ketone or cyclohexanone, an ether such as diethyl ether, diisopropyl ether, tetrahydrofuran, dioxane, dimethoxyethane or diethylene glycol dimethyl ether, an ester such as ethyl acetate or methyl acetate, a halogenated hydrocarbon such as dichloromethane, chloroform or carbon tetrachloride, an aromatic hydrocarbon such as benzene, chlorobenzene, nitrobenzene or toluene, a nitrile such as acetonitrile, or N,N-dimethylformamide, N,N-dimethylacetamide, 1,3-dimethyl-2-imidazolinone or dimethylsulfoxide may, for example, be used. These inert solvents may be used alone or as mixed.

As the base which can be used, an alkali metal hydride such as sodium hydride, an alkali metal alcoholate such as potassium tert-butoxide, or an inorganic salt such as sodium carbonate or potassium carbonate may, for example, be used. The amount of the base may properly be selected within a range of from 1 to 50 equivalents based on the compound [I-b], preferably from 1 to 10 equivalents.

The reaction temperature is within a range of from −70° C. to the boiling point of the inert solvent to be used, preferably within a range of from 0° C. to the boiling point of the inert solvent to be used. The reaction time varies depending upon e.g. the reaction temperature and the reaction amount, but may be selected within a range of from 1 hour to 72 hours in general. After completion of the reaction, the desired product is isolated from the reaction system by a conventional method and may be purified by e.g. column chromatography or recrystallization, as the case requires.

Production process 4

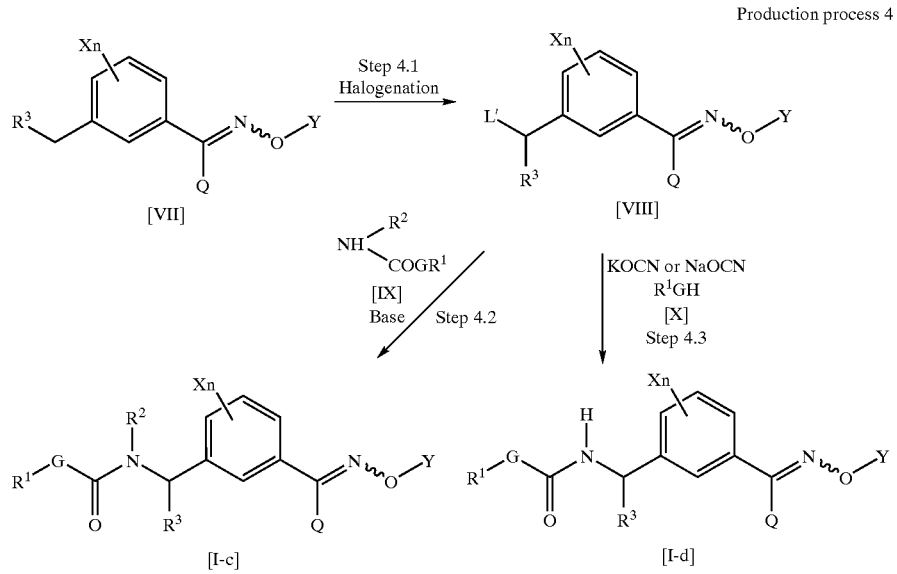

{wherein each of G, Q, $R^1$, $R^2$, $R^3$, X, Y and n is as defined above, and L' is a halogen atom.}

A compound [VIII] can be produced by halogenating a compound [VII] by a known process (see Jikken kagaku Kouza fourth edition, vol. 19, p. 416–482 (The Chemical Society of Japan) for example) (Step 4.1). A compound [I-c] of the present invention can be produced by reacting the compound [VIII] with a compound [IX] in the presence of a base in an inert solvent (Step 4.2). Further, a compound [I-d] of the present invention can be produced by reacting the compound [VIII] with an alkali metal cyanate salt and a compound [X] in an inert solvent (see Journal of the Chemical Society of Japan, vol. 87, No. 5, p. 486 (1966) for example) (Step 4.3).

The halogenating agent which can be used in Step 4.1 of the present production process may, for example, be N-bromosuccinimide, N-chlorosuccinimide or trichloroisocyanuric acid. The amount of the halogenating agent is properly selected within a range of from 0.5 to 10 equivalents based on the compound [VII], preferably from 1 to 3 equivalents. A catalyst such as azobisisobutyronitrile or benzoyl peroxide may be used in the present step, and its amount is properly selected within a range of from 0.001 to 10 equivalents based on the compound [VII], preferably from 0.001 to 1 equivalents.

The inert solvent may be one which does not inhibit the progress of Step 4.1, and a halogenated hydrocarbon such as dichloromethane, chloroform or carbon tetrachloride or an aromatic hydrocarbon such as benzene or chlorobenzene may, for example, be used.

The reaction temperature is within a range of from 0° C. to the boiling point of the inert solvent to be used. The reaction time varies depending upon e.g. the reaction temperature and the reaction amount, but may be selected within a range of from several minutes to 48 hours in general. After completion of the reaction, the desired product is isolated from the reaction system by a conventional method and may be purified by e.g. column chromatography or recrystallization, as the case requires.

With respect to the amount of the material compound [IX] to be used in Step 4.2 of the present production process, it is properly selected within a range of from 1 to 50 equivalents based on the compound [VIII], preferably from 1 to 10 equivalents.

As the base to be used, an inorganic salt such as sodium carbonate, potassium carbonate or sodium hydrogencarbonate or an alkali metal hydride such as sodium hydride may be used, and the amount of the base is properly selected within a range of from 0.5 to 100 equivalents based on the compound [VIII], preferably from 1 to 10 equivalents.

The inert solvent which can be used may be one which does not inhibit the progress of Step 4.2, and a ketone such as acetone, methyl ethyl ketone or cyclohexanone, an ether such as diethyl ether, diisopropyl ether, tetrahydrofuran, dioxane, monoglyme or diglyme, an ester such as ethyl acetate or methyl acetate, a halogenated hydrocarbon such as dichloromethane, chloroform or carbon tetrachloride, an aromatic hydrocarbon such as benzene, chlorobenzene, nitrobenzene or toluene, a nitrile such as acetonitrile, an alcohol such as methanol, ethanol or butanol, or N,N-dimethylformamide, N,N-dimethylacetamide, 1,3-dimethyl 2-imidazolinone or dimethylsulfoxide may, for example, be used, and these inert solvents may be used alone or as mixed.

The reaction temperature is within a range of from –70° C. to the boiling point of the inert solvent to be used, and preferably from –10° C. to the boiling point of the inert solvent to be used. The reaction time varies depending upon e.g. the reaction temperature and the reaction amount, but may be selected within a range of from several minutes to 48 hours in general. After completion of the reaction, the desired product is isolated from the reaction system by a conventional method and may be purified by e.g. column chromatography or recrystallization, as the case requires.

The alkali metal cyanate salt which can be used in Step 4.3 of the present production process may, for example, be potassium cyanate or sodium cyanate. The amount of the metal cyanate salt to be used is properly selected within a range of from 1 to 50 equivalents based on the compound [VIII], preferably from 1 to 10 equivalents, and the compound [X] is properly selected within a range of from 1 to 100 equivalents based on the compound [VIII], preferably from 1 to 20 equivalents. The inert solvent which can be used may be one which does not inhibit the progress of Step 4.3, and a ketone such as acetone, methyl ethyl ketone or cyclohexanone, an ether such as diethyl ether, diisopropyl ether, tetrahydrofuran, dioxane, monoglyme or diglyme, an ester such as ethyl acetate or methyl acetate, a halogenated hydrocarbon such as dichloromethane, chloroform or carbon tetrachloride, an aromatic hydrocarbon such as benzene, chlorobenzene, nitrobenzene or toluene, a nitrile such as acetonitrile, an alcohol such as methanol, ethanol or butanol, or N,N-dimethylformamide, N,N-dimethylacetamide, 1,3-dimethyl-2-imidazolinone or dimethylsulfoxide may, for example, be used, and these inert solvents may be used alone or as mixed.

The reaction temperature is within a range of from 0° C. to the boiling point of the inert solvent to be used. The reaction time varies depending upon e.g. the reaction temperature and the reaction amount, but may be selected within a range of form 1 hour to 48 hours in general. After completion of the reaction, the desired product is isolated from the reaction system by a conventional method and may be purified by e.g. column chromatography or recrystallization, as the case requires.

Production process 5

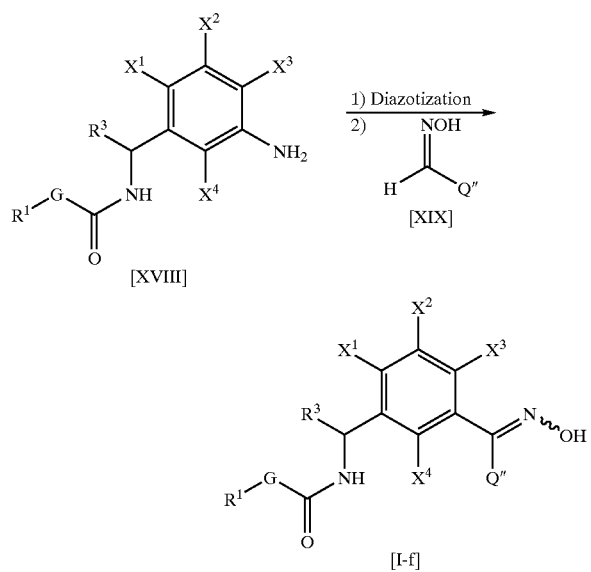

{wherein each of G, $R^1$ and $R^3$ is as defined above, each of $X^1$, $X^2$, $X^3$ and $X^4$ is a hydrogen atom, a halogen atom, a $C_1$–$C_6$ alkyl group, a $C_1$–$C_6$ alkoxy group, a $C_1$–$C_6$ haloalkyl group or a $C_1$–$C_6$ haloalkoxy group, Q" is a hydrogen atom, a haloalkyl group, a $C_1$–$C_6$ alkyl group, a $C_3$–$C_6$ cycloalkyl group or a phenyl group (said group may be substituted by at least one halogen atom, cyano group, nitro group, $C_1$–$C_4$ alkyl group, $C_2$–$C_4$ alkenyl group, $C_2$–$C_4$ alkynyl group, hydroxyl group, $C_1$–$C_4$ alkoxy group, $C_1$–$C_4$ haloalkyl group, $C_1$–$C_4$ haloalkoxy group, $C_1$–$C_4$ alkylcarbonyl group or $C_1$–$C_4$ alkoxycarbonyl group).}

A compound [I-f] of the present invention can be produced by diazotizing a compound [XVIII] by sodium nitrite in the presence of e.g. hydrochloric acid in accordance with a known process, and reacting a compound [XIX] therewith in the presence of e.g. sodium acetate and copper sulfate (see Organic Syntheses vol. 5, p. 139 (1973) for example).

With respect to the amount of the material compound to be used in the present reaction, the compound [XIX] is properly selected within a range of from 1 to 50 equivalents based on the compound [XVIII], preferably from 1 to 5 equivalents.

The solvent which can be used in the present production process may be one which does not inhibit the progress of the present reaction. For example, an ether such as diethyl ether, diisopropyl ether, tetrahydrofuran, dioxane, dimethoxyethane or diethylene glycol dimethyl ether, an ester such as ethyl acetate or methyl acetate, a halogenated hydrocarbon such as dichloromethane, chloroform or carbon tetrachloride, an aromatic hydrocarbon such as benzene, chlorobenzene, nitrobenzene or toluene, an organic acid such as acetic acid or trifluoroacetic acid, or water may, for example, be used, and these solvents may be used alone or as mixed.

As the acid to be used in Step 1) diazotization of the present production process, a strong acid such as sulfuric acid, tetrafluoroboric acid, hydrobromic acid or trifluoroacetic acid may be used instead of the above-mentioned hydrochloric acid. The amount is properly selected within a range of from 1 to 50 equivalents based on the compound [XVIII], preferably from 2 to 4 equivalents. Further, a nitrite ester such as isoamyl nitrite or methyl nitrite may be used instead of the above-mentioned sodium nitrite. The amount is properly selected within a range of from 1 to 50 equivalents based on the compound [XVIII], preferably from 1 to 2 equivalents. The reaction temperature is within a range of from –20° C. to 30° C., preferably within a range of from –5° C. to 5° C. The reaction time varies depending upon e.g. the reaction temperature and the reaction amount, but may be selected within a range of from 30 minutes to 2 hours in general. As the copper compound to be used in Step 2) of coupling in the present reaction, a copper salt such as copper(I) chloride or copper(II) acetate may be used instead of the above-mentioned copper sulfate. The amount is properly selected within a range of from 0.02 to 2 equivalents based on the compound [XVIII], preferably from 0.02 to 0.5 equivalent. Further, the amount of sodium acetate is properly selected within a range of from 1 to 50 equivalents based on the compound [XVIII], preferably from 4 to 10 equivalents. The reaction temperature is within a range of from –20° C. to 30° C., preferably within a range of from –5° C. to 25° C. The reaction time varies depending upon e.g. the reaction temperature and the reaction amount, but may be selected within a range of from 30 minutes to 2 hours in general. After completion of the reaction, the desired product is isolated from the reaction system by a conventional method and may be purified by e.g. column chromatography or recrystallization, as the case requires.

The compound [II] as an intermediate for the compound [I] of the present invention can be produced, for example, in accordance with the following known process, but the process is not limited thereto.

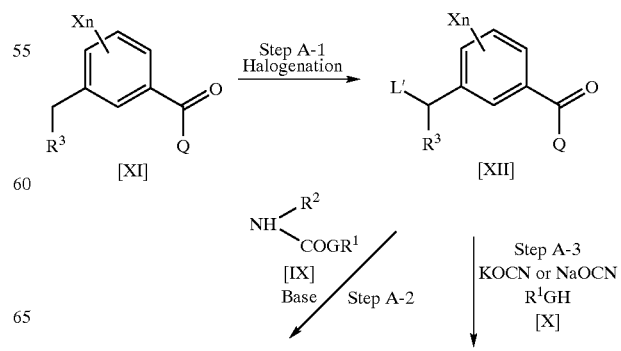

-continued

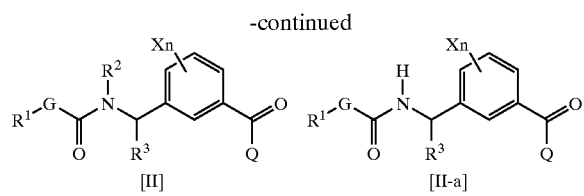

{wherein each of L', G, Q, $R^1$, $R^2$, $R^3$, X and n is as defined above.}

A compound [XII] can be produced by halogenating a compound [XI] (see Jikken kagaku Kouza fourth edition, vol. 19, p. 416–482 (The Chemical Society of Japan) for example) (Step A-1). Further, the intermediate [II] can be produced by reacting the compound [XII] with the compound [IX] in the presence of a base (e.g. an inorganic salt such as sodium carbonate, potassium carbonate or sodium hydrogencarbonate or an alkali metal hydride such as sodium hydride) (Step A-2). Further, an intermediate [II-a] can be produced by reacting the compound [XII] with an alkali metal cyanate salt and the compound [X] in the presence of an inert solvent (see Journal of the Chemical Society of Japan, vol. 87, No. 5, p. 486 (1966) for example) (Step A-3).

The compounds [II] and [IV-a] as intermediates for the compound [I] of the present invention can be produced, for example, in accordance with the following known process, but the process is not limited thereto.

A compound [XIV] can be produced by halogenating a compound [XIII] (see Jikken kagaku Kouza, fourth edition, vol. 19, p. 416–482 (The Chemical Society of Japan) for example) (Step B-1). A compound [XV] can be produced by reacting the compound [XIV] with the compound [X] and an alkali metal cyanate salt (see Journal of the Chemical Society of Japan, vol. 87, No. 5, p. 486 (1966) for example) (Step B-2). Otherwise, the compound [XV] can be produced by reacting the compound [XIV] with the compound [IX] in the presence of an inorganic salt such as sodium carbonate, potassium carbonate or sodium hydrogencarbonate or a base such as an alkali metal hydride such as sodium hydride (Step B-3). A compound [XVI] can be produced by reducing the compound [XV] in accordance with a known process (Jikken kagaku Kouza, fourth edition, vol. 26, p. 159–266 (The Chemical Society of Japan) for example) (B-4). A compound [II-b] can be produced by oxidizing the compound [XVI] in accordance with a known process (see Jikken kagaku Kouza, fourth edition, vol. 21, p. 2–23 (The Chemical Society of Japan) for example) (Step B-5). A compound [XVII] can be produced by halogenating the compound [XVI] in accordance with a known process (see Jikken kagaku Kouza, fourth edition, vol. 19, p. 416–482 (The Chemical Society of Japan) for example) (Step B-6).

A compound [IV-a] can be produced by cyanating the compound [XVII] in accordance with a known process (see Jikken kagaku Kouza, fourth edition, vol. 20, p. 437–462 (The Chemical Society of Japan) for example) (Step B-7).

The compound [VII] as an intermediate for the compound [I] of the present invention can be produced, for example, in

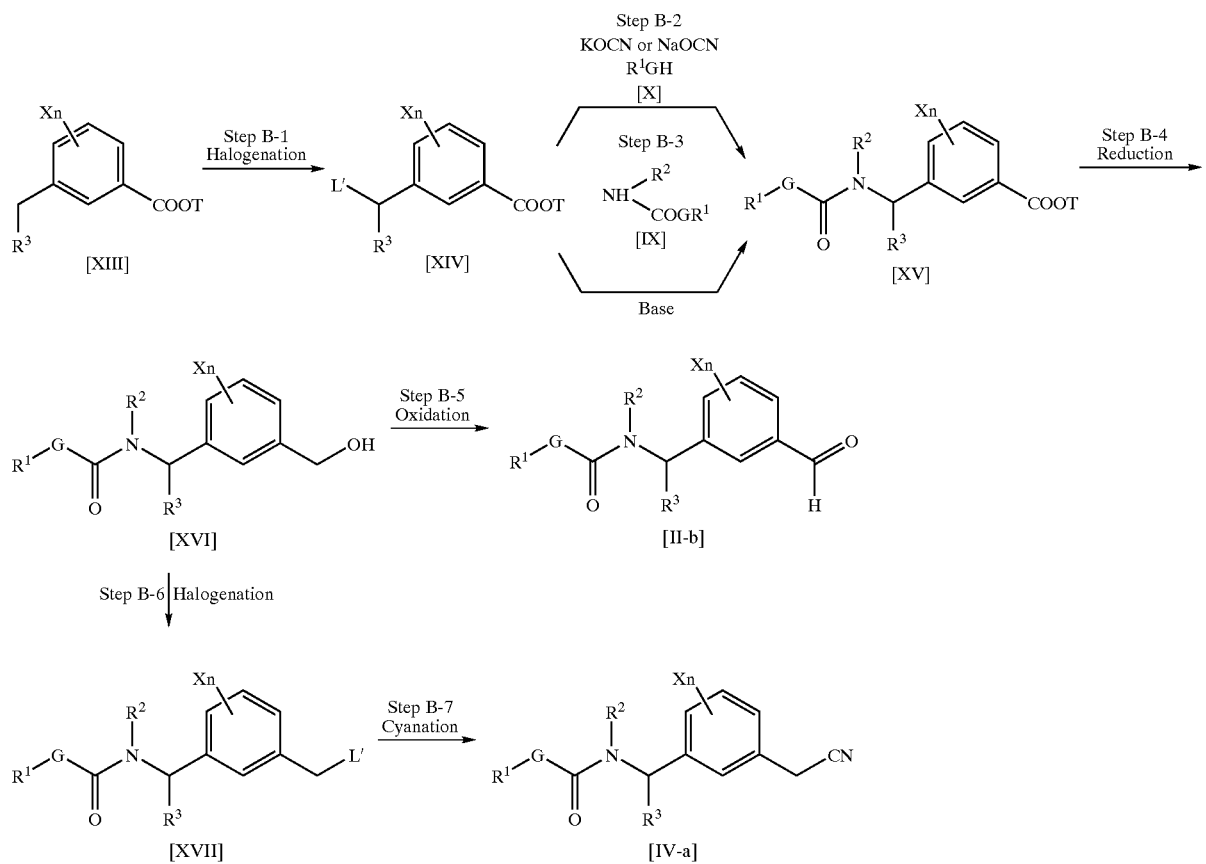

{wherein each of G, Q, $R^1$, $R^2$, $R^3$, X, L' and n is as defined above, and T is a $C_1$–$C_6$ alkyl group.} accordance with the following known process, but the process is not limited thereto.

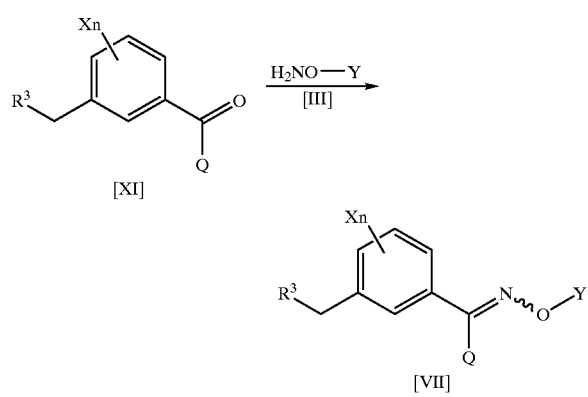

(wherein each of R³, Q, X, Y and n is as defined above.)

The compound [VII] of the present invention can be produced by reacting the compound [XI] and the compound [III] (see Jikken kagaku Kouza, fourth edition, vol. 20, p. 349–355 (The Chemical Society of Japan) for example). Here, the material compound [III] to be used in the present production process may form a salt with e.g. hydrochloric acid or sulfuric acid.

The compound [XVIII] as an intermediate for the compound [I] of the present invention can be produced, for example, in accordance with the following known process, but the process is not limited thereto.

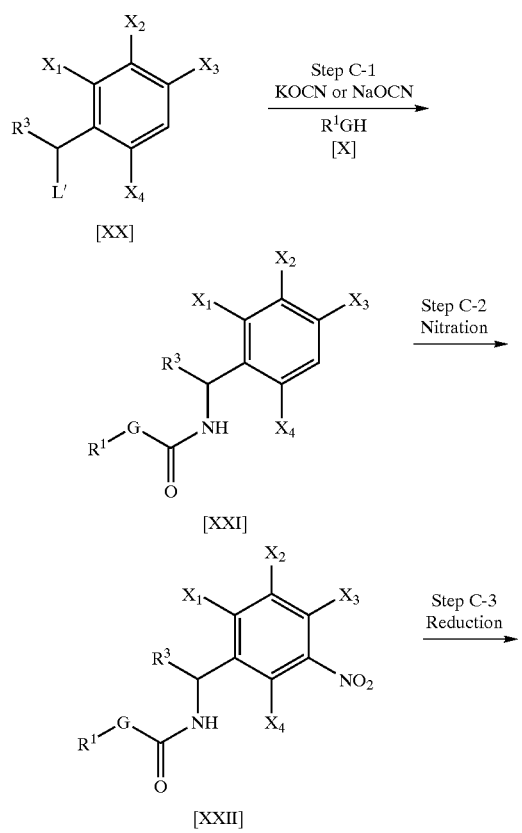

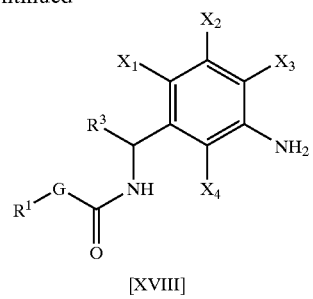

{wherein each of G, R¹, R³, L', X¹, X², X³ and X⁴ is as defined above.}

An intermediate [XXI] can be produced by reacting a compound [XX] with an alkali metal cyanate salt and the compound [X] in an inert solvent (see Journal of the Chemical Society of Japan, vol. 87, No. 5, p. 486 (1966) for example) (Step C-1). An intermediate [XXII] can be produced by nitrating the compound [XXI] with e.g. nitric acid, acetyl nitrate or sodium nitrate (see Jikken kagaku Kouza, fourth edition, vol. 20, p. 394–399 (The Chemical Society of Japan) for example) (Step C-2). The intermediate [XVIII] can be produced by reducing the compound [XXII] in accordance with a known process (see Jikken kagaku Kouza, fourth edition, vol. 26, p. 159–266 (The Chemical Society of Japan) for example) (Step C-3).

EXAMPLES

Now, the processes for producing the compound of the present invention, formulation methods and applications will be specifically described with reference to Examples.

Symbols to be used in the text have the following meanings.

$^1$H-NMR: Proton nuclear magnetic resonance; CDCl₃: Deuterated chloroform; TMS: Tetramethylsilane; s: singlet, d: doublet, t: triplet, q: quartet, quint: quintet, m: multiplet, br: broad, dd: double doublet Preparation Example 1

Preparation of 2-[4-chloro-3-(methoxycarbonylaminomethyl)phenyl]-2-hydroxyiminoacetonitrile (Compound No. A-2)

0.15 g of sodium hydroxide and 0.60 g of methyl N-(2-chloro-5-cyanomethylbenzyl)carbamate were added to 5 ml of ethanol, and 0.40 g of t-butyl nitrite was added to the mixture at room temperature, followed by stirring for 72 hours. After completion of the reaction, the reaction solution was poured into water, extraction with ethyl acetate was carried out, followed by washing with water, and the organic layer was dried over anhydrous magnesium sulfate. The solvent was distilled off under reduced pressure, and the residue was purified by silica gel column chromatography (Wakogel C-200, eluent: hexane/ethyl acetate=3/1) to obtain 0.46 g of 2-[4-chloro-3-(methoxycarbonylaminomethyl)phenyl]-2-hydroxyiminoacetonitrile as a colorless viscous liquid.

$^1$H-NMR: (CDCl₃/TMS, δ (ppm)); 3.72 (s, 3H); 4.48 (d, 2H); 5.43 (br, 1H); 7.43–8.21 (m, 3H); 10.51, 11.15 (br, 1H).

Preparation Example 2

Preparation of 2-[4-chloro-3-(methoxycarbonylaminomethyl)phenyl]-2-methoxyiminoacetonitrile (Compound No. A-3)

0.36 g of 2-[4-chloro-3-(methoxycarbonylaminomethyl)phenyl]-2-hydroxyiminoacetonitrile and 0.54 g of a 28% sodium methylate methanol solution were added to 5 ml of methanol, and 0.49 g of methyl iodide was added thereto, followed by stirring at room temperature for 24 hours. The reaction solution was vacuum concentrated, the solvent was distilled off, water was added to the residue, extraction with ethyl acetate was carried out, and the organic layer was dried over anhydrous magnesium sulfate. The solvent was distilled off under reduced pressure, and the residue was purified by silica gel column chromatography (Wakogel C-200, eluent: hexane/ethyl acetate=4/1–5/1) to obtain 0.18 g of 2-[4-chloro-3-(methoxycarbonylaminomethyl)phenyl]-2-methoxyiminoacetonitrile as colorless crystals (m.p. 104–107° C.)

$^1$H-NMR: (CDCl$_3$/TMS, δ (ppm)); 3.71 (s, 3H); 4.22 (s, 3H); 4.48 (d, 2H); 5.23 (br, 1H); 7.43–8.05 (m, 3H).

Preparation Example 3

Preparation of Methyl N-[2-chloro-5-(1-hydroxyiminoethyl)benzyl]carbamate (Compound No. A-45)

5.0 g of methyl N-(2-chloro-5-acetylbenzyl)carbamate was dissolved in 10 ml of ethanol, and 1.5 g of hydroxylamine hydrochloride, 3.0 g of sodium acetate and 5 ml of water were added thereto, followed by reflux under heating for 4 hours. After completion of the reaction, water was added to the reaction mixture, extraction with ethyl acetate was carried out, the organic layer was dried over anhydrous magnesium sulfate, and the solvent was distilled off under reduced pressure. The obtained crystals were washed with hexane to obtain 5.2 g of methyl N-[2-chloro-5-(1-hydroxyiminoethyl)benzyl]carbamate as colorless crystals (m.p. 124–127° C.).

$^1$H-NMR: (CDCl$_3$/TMS, δ (ppm)); 2.25 (s, 3H); 3.70 (s, 3H); 4.46 (d, 2H); 5.31 (br, 1H); 7.27–7.63 (m, 3H).

Preparation Example 4

Preparation of Methyl N-[3-(1-methoxyiminoethyl)benzyl]carbamate (Compound No. A-40)

0.40 g of methyl N-(3-acetylbenzyl)carbamate was dissolved in 10 ml of ethanol, and 0.36 g of methoxyamine hydrochloride and 5 ml of an aqueous solution of 0.54 g of sodium acetate were added thereto, followed by reflux under heating for 8 hours. After completion of the reaction, water was added to the reaction mixture, extraction with ethyl acetate was carried out, the organic layer was dried over anhydrous magnesium sulfate, and the solvent was distilled off under reduced pressure. The obtained crystals were washed with hexane to obtain 0.40 g of methyl N-[3-(1-methoxyiminoethyl)benzyl]carbamate as a pale yellow oily substance.

$^1$H-NMR: (CDCl$_3$/TMS, δ (ppm)); 2.22 (s, 3H); 3.69 (s, 3H); 3.99 (s, 3H); 4.37 (d, 2H); 5.12 (br, 1H); 7.27–7.56 (m, 4H).

Preparation Example 5

Preparation of Methyl N-{2-chloro-5-[1-(4-fluorobenzyloxyimino)ethyl]benzyl}carbamate (Compound No. A-83)

0.70 g of methyl N-[2-chloro-5-(1-hydroxyiminoethyl)benzyl]carbamate was dissolved in 10 ml of N,N-dimethylformamide, and 0.13 g of 60% sodium hydride was added thereto under cooling with ice, followed by stirring for 1 hour. 0.57 g of 4-fluorobenzyl bromide was dissolved in 2 ml of N,N-dimethylformamide, which was dropwise added to the reaction mixture under cooling with ice. After completion of the dropwise addition, the mixture was stirred at room temperature for 16 hours. After completion of the reaction, the reaction solution was poured into water, extraction with ethyl acetate was carried out, followed by washing with water, and the organic layer was dried over anhydrous magnesium sulfate. The solvent was distilled off under reduced pressure, and the residue was purified by silica gel column chromatography (Wakogel C-200, eluent: hexane/ethyl acetate=5/1) to obtain 0.75 g of methyl N-{2-chloro-5-[1-(4-fluorobenzyloxyimino)ethyl]benzyl}carbamate (m.p. 101–103° C.) as colorless crystals.

$^1$H-NMR: (CDCl$_3$/TMS, δ (ppm)); 2.22 (s, 3H); 3.69 (s, 3H); 4.45 (d, 2H); 5.10 (br, 1H); 5.18 (s, 2H); 7.02–7.65 (m, 7H).

Preparation Example 6

Preparation of Methyl N-[2-chloro-5-(1-hydroxyiminoethyl)benzyl]carbamate (Compound No. A-45)

10.7 g of methyl N-[5-amino-2-chlorobenzyl]carbamate was dissolved in 33 g of 14% hydrochloric acid, followed by stirring at room temperature for 1 hour. 7 ml of an aqueous solution of 3.8 g of sodium nitrite was dropwise added to the solution with stirring at from 0 to 5° C. The formed diazonium salt was dropwise added to a mixed solvent of water/ethyl acetate/toluene (80 ml/40 ml/40 ml) of 21.7 g of sodium acetate, 2.6 g of copper sulfate and 5.9 g of acetaldoxime with vigorously stirring at from 0 to 5° C. over a period of 15 minutes, followed by stirring at room temperature further for 2 hours. The reaction solution was acidified with hydrochloric acid, extraction with ethyl acetate was carried out, followed by washing with water, and the organic layer was dried over anhydrous magnesium sulfate. The solvent was distilled off under reduced pressure, the obtained crude crystals were washed with a mixed solvent of ether/ethyl acetate to obtain 2.8 g of methyl N-[2-chloro-5-(1-hydroxyiminoethyl)benzyl]carbamate as colorless crystals (m.p. 124–127° C.).

$^1$H-NMR: (CDCl$_3$/TMS, δ (ppm)); 2.25 (s, 3H); 3.70 (s, 3H); 4.46 (d, 2H); 5.31 (br, 1H); 7.27–7.63 (m, 3H).

Preparation Example 7

Preparation of Methyl N-{2-methyl-5-[1-(6-methylpyridin-2-yl methoxy)iminoethyl]benzyl}carbamate (Compound No. A-434)

0.43 g of methyl N-[2-methyl-5-(1-hydroxyiminoethyl)benzyl]carbamate was dissolved in 15 ml of N,N-dimethylformamide, 0.75 g of potassium carbonate and 0.32 g of 2-chloro-6-methylpyridine hydrochloride were added thereto, followed by stirring under heating at from 90 to 100° C. for 8 hours. After completion of the reaction, the reaction solution was poured into water, extraction with ethyl acetate was carried out, followed by washing with water, and the organic layer was dried over anhydrous magnesium sulfate. The solvent was distilled off under reduced pressure, and the residue was purified by silica gel column chromatography (Wakogel C-200, eluent: hexane/ethyl acetate=4/1) to obtain 0.30 g of methyl N-{2-methyl-5-[1-(6-methylpyridin-2-yl methoxy)iminoethyl]benzyl}carbamate (m.p. 72–75° C.) as pale yellow crystals.

$^1$H-NMR: (CDCl$_3$/TMS, δ (ppm)); 2.30 (s, 3H); 2.32 (s, 3H); 2.56 (s, 3H); 3.69 (s, 3H); 4.35 (d, 2H); 4.94 (br, 1H); 5.33 (s, 2H); 7.04–7.59 (m, 6H).

Now, $^1$H-NMR(CDCl$_3$/TMS, δ (ppm)) data of some among examples of the compound of the present invention, will be shown in Tables 14 to 20.

TABLE 14

| Comp. No. | $^1$H—NMR δ value (ppm) Solvent CDCl$_3$/TMS |
|---|---|
| A-2 | 3.72(s, 3H); 4.48(d, 2H); 5.43(br, 1H); 7.43–8.21(m, 3H) |
| A-37 | 2.20, 2.25(s, 3H); 3.70(s, 3H); 4.37(d, 2H); 4.54, 4.71(d, 2H); 5.08(br, 1H); 5.20–5.38(m, 2H); 6.00–6.11(m, 1H); 7.29–7.56(m, 4H) |
| A-38 | 2.17, 2.25(s, 3H); 3.68(s, 3H); 4.35(d, 2H); 5.05(br, 1H); 5.09, 5.24(s, 2H); 7.28–7.55(m, 9H) |
| A-39 | 1.24, 1.33(t, 3H); 2.18, 2.22(s, 3H); 3.69(s, 3H); 4.09, 4.24(q, 2H); 4.37(d, 2H); 5.14(br, 1H); 7.26–7.56(m, 4H) |
| A-40 | 2.22(s, 3H); 3.69(s, 3H); 3.99(s, 3H); 4.37(d, 2H); 5.12(br, 1H); 7.27–7.56(m, 4H) |
| A-41 | 3.67(s, 3H); 4.35(dd, 2H); 4.66–4.69(m, 2H); 5.17(br, 1H); 5.95–6.08(m, 2H); 7.25–7.48(m, 9H) |
| A-42 | 3.67(s, 3H); 3.96(s, 3H); 4.11(dd, 2H); 5.30(br, 1H); 7.25–7.80(m, 9H) |
| A-43 | 1.27, 1.29(t, 3H); 3.67(s, 3H); 4.22, 4.23(q, 2H); 4.34(dd, 2H); 5.15(br, 1H); 7.27–7.48(9H) |
| A-50 | 0.98(t, 3H); 1.75(quint, 2H); 2.21(s, 3H); 3.69(s, 3H); 4.15(t, 2H); 4.46(d, 2H); 5.19(br, 1H); 7.34(d, 1H); 7.51(d, 1H); 7.66(s, 1H) |
| A-51 | 1.30(d, 6H); 2.19(s, 3H); 3.69(s, 3H); 4.41–4.49(m, 3H); 5.20(br, 1H); 7.34(d, 1H); 7.52(dd, 1H); 7.65(s, 1H) |
| A-53 | 0.95(t, 3H); 1.27(d, 3H); 1.52–1.78(m, 2H); 2.19(s, 3H); 3.68(s, 3H); 4.21–4.28(m, 1H); 4.44(d, 2H); 5.27(br, 1H); 7.30–7.65(m, 3H) |
| A-54 | 0.96(d, 6H); 2.04(m, 1H); 2.21(s, 3H); 3.68(s, 3H); 3.96(d, 2H); 4.45(d, 2H); 5.24(br, 1H); 7.33(d, 1H); 7.50(dd, 1H); 7.65(s, 1H) |
| A-55 | 1.35(t, 9H); 2.18(d, 3H); 3.69(s, 3H); 4.45(d, 2H); 5.20(br, 1H); 7.27–7.63(m, 3H) |

TABLE 15

| Comp. No. | $^1$H—NMR δ value (ppm) Solvent CDCl$_3$/TMS |
|---|---|
| A-56 | 0.30–0.35(m, 2H); 0.54–0.60(m, 2H); 1.14–1.27(m, 1H); 2.23(s, 3H); 3.69(s, 3H); 4.01(d, 2H); 4.45(d, 2H); 5.20(br, 1H); 7.34(d, 1H); 7.51(dd, 1H); 7.66(s, 1H) |
| A-62 | 2.05(quint, 2H); 2.21(s, 3H); 2.74(t, 2H); 3.69(s, 3H); 4.22(t, 2H); 4.46(d, 2H); 5.18(br, 1H); 7.17–7.67(m, 8H) |
| A-63 | 1.29(t, 3H); 2.29(s, 3H); 3.69(s, 3H); 4.25(q, 2H); 4.47(d, 2H); 4.73(s, 2H); 5.22(br, 1H); 7.34(d, 1H); 7.50(dd, 1H); 7.64(s, 1H) |
| A-64 | 1.49(s, 9H); 2.28(s, 3H); 3.69(s, 3H); 4.46(d, 2H); 4.63(s, 2H); 5.19(br, 1H); 7.35(1H); 7.5(dd, 1H); 7.64(br, 1H) |
| A-91 | 2.25(s, 3H); 2.39(s, 3H); 3.70(s, 3H); 4.45(d, 2H); 5.22(s, 2H); 5.31(br, 1H); 7.13–7.54(m, 7H) |
| A-94 | 2.24(s, 3H); 3.69(s, 3H); 3.82(s, 3H); 4.45(d, 2H); 5.19(br, 1H); 5.21(s, 3H); 6.84–7.66(m, 7H) |
| A-95 | 2.21(s, 3H); 3.70(s, 3H); 3.81(s, 3H); 4.45(d, 2H); 5.16(s, 3H); 5.21(br, 1H); 6.89–7.66(m, 7H) |
| A-98 | 1.33, 1.35(s, 9H); 2.23, 2.24(s, 3H); 3.69(s, 3H); 4.45(d, 2H); 5.21, 5.23(s, 2H); 5.26(br, 1H); 7.32–7.67(m, 7H) |
| A-100 | 2.25(s, 3H); 3.68(s, 3H); 4.44(d, 2H); 5.22(br, 1H); 5.27(s, 2H); 7.32–7.65(m, 7H) |
| A-150 | 2.23(s, 3H); 2.40(s, 3H); 3.69(s, 3H); 4.46(d, 2H); 5.18(br, 1H); 5.24(s, 2H); 7.30–7.49(m, 7H) |
| A-155 | 2.22(s, 3H); 2.36(s, 3H); 2.39(s, 3H); 3.67(s, 3H); 4.44(d, 2H); 5.20(br, 1H); 5.21(s, 2H); 7.10–7.48(m, 6H) |
| A-158 | 2.20(s, 3H); 2.40(s, 3H); 2.39(s, 3H); 3.69(s, 3H); 3.81(s, 3H); 4.46(d, 2H); 5.15(br, 1H + s, 2H); 6.89–7.49(m, 6H) |
| A-189 | 1.39, 1.74(d, 3H); 2.21(s, 3H); 3.69(s, 3H); 4.46(d, 2H); 4.63, 4.77(d, 2H); 5.14–5.29(br, 1H); 5.67–6.03(m, 2H); 7.33–7.65(m, 3H) |
| A-198 | 2.20(s, 3H); 2.48(q, 2H); 3.69(s, 3H); 4.24(t, 2H); 4.46(d, 2H); 5.05–5.16(m, 2H); 5.20(br, 1H); 5.80–5.94(m, 1H); 7.33–7.66(m, 3H) |

TABLE 16

| Comp. No. | $^1$H—NMR δ value (ppm) Solvent CDCl$_3$/TMS |
|---|---|
| A-206 | 2.17(s, 3H); 3.68(s, 3H); 4.44(d, 2H); 5.09(s, 2H); 5.23(br, 1H); 7.26–7.53(m, 8H) |
| A-207 | 2.18(s, 3H); 3.68(s, 3H); 4.46(d, 2H); 5.17(br, 1H); 5.20(s, 2H); 7.22–7.56(m, 7H) |
| A-215 | 2.21(s, 3H); 3.69(s, 3H); 4.46(d, 2H); 5.17(br, 1H); 5.69(s, 2H); 7.26–8.18(m, 10H) |
| A-216 | 1.61(d, 3H); 2.26(s, 3H); 4.43(d, 2H); 5.15(br, 1H); 5.37(q, 1H); 7.26–7.60(m, 8H) |
| A-219 | 2.25(br, 3H); 3.75, 3.79(s, 3H); 4.53(br, 4H); 5.47, 5.53(s, 2H); 7.19–7.78(m, 1H) |
| A-229 | 2.20(s, 3H); 2.56(t, 4H); 2.75(t, 2H); 3.69(s, 3H); 3.73(t, 4H); 4.34(t, 2H); 4.45(d, 2H); 5.34(br, 1H); 7.28–7.65(m, 3H) |

TABLE 16-continued

| Comp. No. | ¹H—NMR δ value (ppm) Solvent CDCl₃/TMS |
|---|---|
| A-234 | 2.32(s, 3H); 2.68(t, 2H); 3.68(s, 3H); 4.30(t, 2H); 4.45(d, 2H); 5.40(br, 1H); 7.33–7.65(m, 3H) |
| A-240 | 2.24(s, 3H); 2.68(m, 1H); 2.87(m, 1H); 3.32(m, 1H); 3.69(s, 3H); 4.08–4.47(m, 2H); 4.46(d, 2H); 5.23(br, 1H); 7.35(d, 1H); 7.51(dd, 1H); 7.66(s, 1H) |
| A-241 | 2.24(s, 3H); 3.69(s, 3H); 3.90–4.05(m, 4H); 4.25(d, 2H); 4.45(d, 2H); 5.25(t, br, 2H); 7.34(d, 1H); 7.51(dd, 1H); 7.65(s, 1H) |
| A-251 | 0.89(t, 3H); 1.23–1.41(m, 8H); 1.71(quintet, 2H); 2.19(s, 3H); 3.68(s, 3H); 4.17(q, 2H); 4.45(d, 2H); 5.23(br, 1H); 7.34(dd, 1H); 7.51(dd, 1H); 7.65(s, 1H) |
| A-266 | 2.27(s, 3H); 3.68(s, 3H); 4.44(d, 2H); 5.25(br, 1H); 5.31(s, 2H); 7.33–8.27(m, 7H) |
| A-269 | 2.25(s, 3H); 2.62(s, 3H); 3.69(s, 3H); 4.46(d, 2H); 5.22(br, 1H); 5.28(s, 2H); 7.33–8.01(m, 7H) |
| A-273 | 1.30(d, 6H); 3.70(s, 3H); 4.41–4.49(m, 3H); 5.18(br, 1H); 7.35(d, 1H); 7.62(dd, 1H); 7.57(s, 1H); 8.00(s, 1H) |
| A-286 | 2.29(s, 3H); 2.56(s, 3H); 3.67(s, 3H); 4.44(d, 2H); 5.33(br, 3H); 7.05(d, 1H); 7.19(d, 3H); 7.32(d, 1H); 7.49–7.64(m, 3H) |

TABLE 17

| Comp. No. | ¹H—NMR δ value (ppm) Solvent CDCl₃/TMS |
|---|---|
| A-289 | 3.17(s, 3H); 3.69(s, 3H); 4.48(d, 2H); 5.18(br, 1H); 5.35(s, 2H); 7.27–7.69(m, 7H) |
| A-290 | 3.17(s, 3H); 3.68(s, 3H); 4.49(d, 2H); 5.26(br, 1H); 5.37(s, 2H); 7.24–7.77(m, 6H); 8.60(d, 1H) |
| A-291 | 2.23(s, 3H); 3.69(s, 3H); 4.00(s, 3H); 4.45(d, 2H); 5.19(br, 1H); 5.24(s, 2H); 7.33–7.68(m, 7H) |
| A-292 | 1.18(t, 3H); 2.21(s, 3H); 2.81(q, 2H); 3.69(s, 3H); 4.46(d, 2H); 4.67(s, 2H); 5.18(br, 1H); 7.36d, 1H); 7.50(dd, 1H); 7.65(s, 1H) |
| A-293 | 1.09–1.22(m, 3H); 1.92(s, 3H); 2.70–2.79(m, 2H); 3.69(s, 3H); 3.85, 3.90(s, 3H); 4.46(d, 2H); 4.68, 4.99(s, 2H); 5.17(br, 1H); 7.34–7.64(m, 3H) |
| A-297 | 1.41(t, 3H); 2.79(q, 2H); 3.68(s, 3H); 4.45(d, 2H); 5.20(br, 1H); 5.43(s, 2H); 7.33–7.73(m, 7H) |
| A-298 | 1.17(t, 3H); 1.43(d, 3H); 2.19(s, 3H); 2.80(q, 2H); 3.70(s, 3H); 4.45(d, 2H); 4.65(q, 1H); 5.17(br, 1H); 7.35(d, 1H); 7.50(dd, 1H); 7.62(s, 1H) |
| A-299 | 1.09–1.16(m, 3H); 1.38, 1.43(d, 3H); 1.82, 1.83(s, 3H); 2.68, 2.82(m, 2H); 3.69(s, 3H); 3.84, 3.88(s, 3H); 4.45(d, 2H); 4.84, 5.64(q, 1H); 5.21(br, 1H); 7.34(d, 1H); 7.49(d, 1H); 7.61(s, 1H) |
| A-300 | 1.09–1.16(m, 3H); 1.23–1.29(m, 3H); 1.38, 1.42(d, 3H); 1.83(s, 3H); 2.68–2.82(m, 2H); 3.69(s, 3H); 4.03–4.16(m, 2H); 4.45(d, 2H); 4.84, 5.54(q, 1H); 5.21(br, 1H); 7.34(dd, 1H); 7.52(dd, 1H); 7.65(s, 1H) |
| A-303 | 1.11(t, 3H); 2.75(q, 2H); 3.69(s, 3H); 4.45(d, 2H); 5.22(br, 3H); 7.28–7.65(m, 8H) |
| A-304 | 1.12(t, 3H); 2.76(q, 2H); 3.69(s, 3H); 3.82(s, 3H); 4.46(d, 2H); 5.20(br, 3H); 3.84(dd, 1H); 6.95–6.99(m, 2H); 7.25–7.36(m, 2H); 7.50(dd, 1H); 7.65(s, 1H) |
| A-305 | 1.17(t, 3H); 2.82(q, 2H); 3.68(s, 3H); 4.45(d, 2H); 5.18(br, 1H); 5.36(s, 2H); 7.19–7.73(m, 6H); 8.59(d, 1H) |
| A-309 | 1.59(d, 3H); 3.00(s, 3H); 3.68(s, 3H); 4.43(d, 2H); 5.14(br, 1H); 5.75(q, 1H); 7.16–7.59(m, 7H) |
| A-310 | 1.58(d, 3H); 2.25(s, 3H); 3.67(s, 3H); 4.42(d, 2H); 5.21(br, 1H); 5.32(q, 1H); 7.24–7.59(m, 7H) |

TABLE 18

| Comp. No. | ¹H—NMR δ value (ppm) Solvent CDCl₃/TMS |
|---|---|
| A-312 | 1.49, 1.60(d, 3H); 2.26(s, 3H); 3.68(s, 3H); 3.81(s, 3H); 4.43(d, 2H); 5.15(br, 1H); 5.34(q, 1H); 6.81(dd, 1H); 6.92–6.97(m, 2H); 7.24–7.32(m, 2H); 7.48(dd, 1H); 7.60(s, 1H) |
| A-313 | 1.62(d, 3H); 2.27(s, 3H); 3.68(s, 3H); 4.43(d, 2H); 4.43(d, 2H); 5.15(br, 1H); 5.40(q, 1H); 7.30–7.61(m, 7H) |
| A-315 | 2.49(s, 3H); 2.33(s, 3H); 3.70(s, 3H); 3.82(s, 3H); 4.37(d, 2H); 4.86(br, 1H); 5.21(s, 2H); 6.83–7.53(m, 7H) |
| A-322 | 2.23(br, 6H); 3.74–3.81(br, 9H); 4.33–4.54(br, 4H); 5.21(s, 2H); 6.68–7.48(m, 11H) |
| A-329 | 2.25(s, 3H); 3.69(s, 3H); 3.82(s, 3H); 4.41(d, 2H); 5.07(br, 1H); 5.20(s, 2H); 6.84–7.63(m, 7H) |
| A-332 | 2.29(s, 3H); 3.69(s, 3H); 4.46(d, 2H); 5.26(br, 1H); 5.37(s, 2H); 7.19–7.73(m, 5H); 8.60(d, 1H) |
| A-333 | 2.31(s, 3H); 2.33(s, 3H); 3.70(s, 3H); 4.37(d, 2H); 4.86(br, 1H); 5.36(s, 2H); 7.15–7.72(m, 6H); 8.59(d, 1H) |
| A-338 | 2.30(s, 3H); 3.71(s, 3H); 4.38(d, 2H); 4.99(br, 1H); 5.36(s, 2H); 7.22–7.56(m, 8H) |
| A-339 | 2.27(s, 3H); 3.71(s, 3H); 4.38(d, 2H); 5.00(br, 1H); 5.21(s, 2H); 7.26–7.54(m, 8H) |

TABLE 18-continued

| Comp. No. | ¹H—NMR δ value (ppm) Solvent CDCl₃/TMS |
|---|---|
| A-341 | 0.60–0.70(m, 2H); 0.93–0.99(m, 2H); 2.19–2.28(m, 1H); 3.69(s, 3H); 4.44(d, 2H); 5.14(br, 1H); 5.32(s, 2H); 7.21–7.55(m, 7H) |
| A-343 | 2.25(s, 3H); 2.40(s, 3H); 3.70(s, 3H); 4.37(d, 2H); 5.03(br, 1H); 5.26(s, 2H); 7.17–7.56(m, 8H) |
| A-344 | 2.25(s, 3H); 2.37(s, 3H); 3.70(s, 3H); 4.37(d, 2H); 5.04(br, 1H); 5.20(s, 2H); 7.11–7.56(m, 8H) |
| A-348 | 2.30(s, 3H); 3.69(s, 3H); 4.37(d, 2H); 5.06(br, 1H); 5.45(s, 2H); 7.26–7.68(m, 8H) |
| A-349 | 2.27(s, 3H); 3.69(s, 3H); 4.37(d, 2H); 5.07(br, 1H); 5.27(s, 2H); 7.25–7.67(m, 8H) |

TABLE 19

| Comp. No. | ¹H–NMR δ value (ppm) Solvent CDCl₃/TMS |
|---|---|
| A-350 | 2.27(s, 3H); 3.68(s, 3H); 4.35(d, 2H); 5.11(br, 1H); 5.28(s, 2H); 7.25–7.62(m, 8H) |
| A-361 | 2.23, 2.27(s, 6H); 3.79(s, 3H); 4.50–4.75(br, 4H); 5.40(s, 2H); 7.11–7.70(m, 11H) |
| A-366 | 2.21(br, 6H); 3.80(s, 3H); 4.25–4.52(br, 4H); 5.18(s, 2H); 7.13–7.45(m, 11H) |
| A-368 | 1.93(s, 3H); 2.22, 2.24(s, 3H); 2.34(s, 3H); 3.70(s, 3H); 3.84, 3.90(s, 3H); 4.33(d, 2H); 4.69, 5.00(s, 2H); 4.89(br, 1H); 7.17(d, 1H); 7.46(d, 1H); 7.52(s, 1H) |
| A-369 | 2.19(s, 3H); 2.34(s, 3H); 3.04(t, 2H); 3.70(s, 3H); 4.32–4.41(m, 4H); 4.86(br, 1H); 7.16–7.52(m, 8H) |
| A-373 | 2.22(s, 3H); 2.35(s, 3H); 3.69(s, 3H); 4.41(d, 2H); 5.07(br, 1H); 5.18(s, 2H); 6.96–7.63(m, 7H) |
| A-378 | 1.58(d, 3H); 2.30(s, 3H); 3.68(s, 3H); 4.89(d, 2H); 5.05(br, 1H); 5.74(q, 1H); 6.96–7.57(m, 7H) |
| A-379 | 1.58(d, 3H); 2.26(s, 3H); 3.68(s, 3H); 4.39(d, 2H); 5.05(br, 1H); 5.31(q, 1H); 6.97–7.57(m, 7H) |
| A-383 | 0.61, 0.92(m, 4H); 2.21(m, 1H); 3.69(s, 3H); 4.44(d, 2H); 5.14(br, 1H); 5.21(s, 2H); 7.26–7.47(m, 8H) |
| A-394 | 2.32(s, 3H); 3.68(s, 3H); 4.44(d, 2H); 5.18(br, 1H); 5.42(s, 2H); 7.31–7.98(m, 8H) |
| A-398 | 2.26(s, 3H); 3.70(s, 3H); 4.38(d, 2H); 5.00(br, 1H); 5.31(s, 2H); 7.04–7.56(m, 8H) |
| A-399 | 2.27(s, 3H); 3.70(s, 3H); 4.38(d, 2H); 5.01(br, 1H); 5.23(s, 2H); 6.96–7.55(m, 8H) |
| A-400 | 1.90(s, 6H); 2.26(s, 3H); 3.68(s, 3H); 3.89(s, 6H); 4.43(d, 2H); 5.26(s, 2H); 5.41(br, 1H); 7.32–7.63(m, 3H) |
| A-405 | 0.66, 0.97(m, 4H); 2.28(m, 1H); 3.69(s, 3H); 4.43(d, 2H); 5.16(br, 1H); 5.34(s, 2H); 7.18–7.74(m, 6H); 8.58(d, 1H) |

TABLE 20

| Comp. No. | ¹H—NMR δ value (ppm) Solvent CDCl₃/TMS |
|---|---|
| A-406 | 1.58(d, 3H); 2.25(s, 3H); 2.39(s, 3H); 3.69(s, 3H); 4.41(d, 2H); 5.19(br, 1H); 5.58(q, 1H); 7.15–7.60(m, 7H) |
| A-407 | 1.59(d, 3H); 2.25(s, 3H); 2.36(s, 3H); 3.68(s, 3H); 4.42(d, 2H); 5.17(br, 1H); 5.33(q, 1H); 7.07–7.60(m, 7H) |
| A-408 | 1.59(d, 3H); 2.24(s, 3H); 2.34(s, 3H); 3.68(s, 3H); 4.43(d, 2H); 5.16(br, 1H); 5.33(q, 1H); 7.14–7.60(m, 7H) |
| A-412 | 1.90(s, 6H); 2.26(s, 3H); 3.68(s, 3H); 3.89(s, 6H); 4.43(d, 2H); 5.26(s, 1H); 5.41(br, 1H); 7.33(d, 1H); 7.52(dd, 1H); 7.62(d, 1H) |
| A-420 | 2.32(s, 3H); 2.57(s, 3H); 3.70(s, 3H); 4.37(d, 2H); 5.05(br, 1H); 5.34(s, 2H); 7.04–7.60(m, 7H) |
| A-428 | 2.26(s, 3H); 3.68(s, 3H); 4.41(d, 2H); 5.15(br, 1H); 5.24(s, 2H); 7.00–8.21(m, 7H) |
| A-429 | 2.29(s, 3H); 2.38(s, 3H); 2.56(s, 3H); 3.67(s, 3H); 4.44(d, 2H); 5.27(br, 1H); 5.33(s, 2H); 7.06(d, 1H); 7.19(d, 1H); 7.47(br, 2H); 7.57(t, 1H) |
| A-430 | 2.30(s, 3H); 2.56(s, 3H); 3.68(s, 3H); 4.41(d, 2H); 5.15(br, 1H); 5.32(s, 2H); 6.98–7.62(m, 6H) |
| A-435 | 2.26(s, 3H); 2.40(s, 3H); 2.88, 2.95(br, 3H); 3.71, 3.76(br, 3H); 4.63, 4.67(br, 2H); 5.35(s, 2H); 7.22–7.47(m, 6H) |
| A-439 | 2.57(s, 3H); 3.69(s, 3H); 4.44(d, 2H); 5.30(br, 3H); 7.06–7.61(m, 6H); 8.16(s, 1H) |
| A-440 | 2.31(s, 3H); 3.64(s, 3H); 4.37(d, 2H); 5.37(br, 1H); 5.52(s, 2H); 6.94–8.27(m, 9H) |
| A-443 | 1.62–2.09(m, 4H); 2.23(s, 3H); 3.69(s, 3H); 3.78–3.97(m, 2H); 4.15–4.30(m, 3H); 4.45(d, 2H); 5.06–5.23(br, 1H); 7.33–7.65(m, 3H) |
| A-445 | 1.40(t, 3H); 2.25(s, 3H); 3.05(q, 2H); 3.69(s, 3H); 4.46(d, 2H); 5.20(br, 1H); 5.31(s, 2H); 7.13–7.66(m, 4H) |

Now, Preparation Examples of intermediates for the synthesis of the compound of the present invention will be shown below as Reference Examples.

Reference Example 1

Preparation of Methyl 4-chloro-3-(methoxycarbonylaminomethyl)benzoate 40.4 g of methyl 4-chloro-3-methylbenzoate, 39 g of N-bromosuccinimide and 1 g of azobisisobutyronitrile were added to 300 ml of carbon tetrachloride, followed by reflux under heating for 4 hours. After completion of the reaction, the reaction mixture was cooled to room temperature, insoluble matters were collected by filtration and the filtrate was concentrated. The obtained crude crystals were washed with hexane to obtain 34.3 g of methyl 3-bromomethyl-4-chlorobenzoate as white crystals.

16.0 g of the obtained methyl 3-bromomethyl-4-chlorobenzoate, 15.0 g of potassium cyanate and 35 ml of methanol were added to 200 ml of N,N-dimethylformamide, followed by stirring at 90° C. for 4 hours. After completion of the reaction, water was added to the reaction mixture, extraction with ethyl acetate was carried out, and the organic layer was dried over anhydrous magnesium sulfate. The solvent was distilled off under reduced pressure, and the obtained crude crystals were washed with isopropanol to obtain 25.2 g of methyl 4-chloro-3-(methoxycarbonylaminomethyl)benzoate as white crystals.

$^1$H-NMR: (CDCl$_3$/TMS, δ (ppm)); 3.70 (s, 3H); 3.90 (s, 3H); 4.48 (d, 2H); 5.29 (br, 1H); 7.43 (d, 1H); 7.89 (dd, 1H); 8.05 (s, 1H).

Reference Example 2

Preparation Process of Methyl N-(2-chloro-5-hydroxymethylbenzyl)carbamate 10.3 g of methyl 4-chloro-3-(methoxycarbonylaminomethyl)benzoate was dissolved in 80 ml of anhydrous tetrahydrofuran, 100 ml of diisobutylaluminum hydride (0.95 M hexane solution) was dropwise added thereto in an atmosphere of nitrogen at from –50° C. to –30° C., and after completion of the dropwise addition, the mixture was stirred at room temperature for 16 hours. After completion of the reaction, diluted hydrochloric acid was dropwise added to the reaction mixture at 0° C., water was added thereto, extraction with ethyl acetate was carried out, and the organic layer was dried over anhydrous magnesium sulfate. The solvent was distilled off under reduced pressure, and the residue was purified by silica gel column chromatography (Wakogel C-200, eluent: hexane/ethyl acetate=1/1) to obtain 6.5 .g of methyl N-(2-chloro-5-hydroxymethylbenzyl)carbamate as white crystals.

$^1$H-NMR: (CDCl$_3$/TMS, δ (ppm)); 2.20 (br, 1H); 3.67 (s, 3H); 4.43 (d, 2H); 4.65 (s, 2H); 5.26 (br, 1H); 7.21–7.37 (m, 3H).

Reference Example 3

Preparation Process of Methyl N-(5-bromomethyl-2-chlorobenzyl)carbamate 6.2 g of methyl N-(2-chloro-5-hydroxymethylbenzyl)carbamate was dissolved in 50 ml of ethylene glycol dimethyl ether, and 2.7 g of phosphorus tribromide was dropwise added to this solution at –20° C., followed by stirring at room temperature for 1 hour. After completion of the reaction, water was added to the reaction solution, extraction with ethyl acetate was carried out, followed by washing with an aqueous sodium hydrogencarbonate solution, and the organic layer was dried over anhydrous magnesium sulfate. The solvent was distilled off under reduced pressure to obtain 6.1 g of methyl N-(5-bromomethyl-2-chlorobenzyl)carbamate as white crystals.

$^1$H-NMR: (CDCl$_3$/TMS, δ (ppm)); 3.70 (s, 3H); 4.37 (d, 2H); 4.49 (s, 2H); 5.20 (br, 1H); 7.25–7.40 (m, 3H).

Reference Example 4

Preparation of Methyl N-(2-chloro-5-cyanomethylbenzyl)carbamate 2.3 g of the methyl N-(5-bromomethyl-2-chlorobenzyl)carbamate obtained in Reference Example 3 was dissolved in 20 ml of N,N-dimethylformamide, and 0.43 g of sodium cyanide was added thereto at 0° C. Stirring was carried out at 0° C. for 1 hour, and stirring was carried out further for 4 hours at room temperature, then water was added to the reaction mixture, extraction with ethyl acetate was carried out, and the organic solvent was dried over anhydrous magnesium sulfate. The solvent was distilled off under reduced pressure, and the obtained crude crystals were washed with hexane to obtain 1.3 g of methyl N-(2-chloro-5-cyanomethylbenzyl)carbamate as white crystals.

$^1$H-NMR: (CDCl$_3$/TMS, δ (ppm)); 3.70 (s, 3H); 3.73 (s, 2H); 4.44 (d, 2H); 5.21 (br, 1H); 7.24–7.40 (m, 3H).

Reference Example 5

Preparation of Methyl N-(2-chloro-5-acetylbenzyl)carbamate 25.0 g of 4-chloro-3-methylacetophenone, 26.6 g of N-bromosuccinic imide and a catalytic amount of azobisisobutyronitrile were added to 150 ml of carbon tetrachloride, followed by reflux under heating for 2 hours. After completion of the reaction, the reaction mixture was cooled to room temperature, insoluble matters were collected by filtration, and the filtrate was concentrated under reduced pressure. The obtained residue, 18.0 g of potassium cyanate and 38 ml of methanol were added to 150 ml of N,N-dimethylformamide, followed by stirring at 90° C. for 4 hours. After completion of the reaction, water was added to the reaction mixture, extraction with ethyl acetate was carried out, and the organic layer was dried over anhydrous magnesium sulfate. The solvent was distilled off under reduced pressure, and the obtained residue was purified by silica gel column chromatography (Wakogel C-200, eluent: hexane/ethyl acetate) and washed with isopropyl ether to obtain 6.8 g of methyl N-(2-chloro-5-acetylbenzyl)carbamate as colorless crystals.

$^1$H-NMR: (CDCl$_3$/TMS, δ (ppm)); 2.59 (s, 3H); 3.70 (s, 3H); 4.50 (d, 2H); 5.31 (br, 1H); 7.46 (d, 1H); 7.81 (dd, 1H); 7.97 (s, 1H).

Reference Example 6

Preparation of Methyl N-(2-chloro-5-acetylbenzyl)carbamate 25.0 g of 4-chloro-3-methylacetophenone and 13.9 g of trichloroisocyanuric acid were suspended in 150 ml of chlorobenzene. A catalytic amount of azobisisobutyronitrile was added thereto, followed by stirring under heating at from 85 to 90° C. for 12 hours. After completion of the reaction, the reaction mixture was cooled to room temperature, and insoluble matters were collected by filtration. The filtrate was washed with an aqueous sodium hydroxide solution and water in this order, and the organic layer was dried over anhydrous magnesium sulfate. The solvent was distilled off under reduced pressure, and the obtained residue, 12.2 g of potassium cyanate and 14.4 g of methanol were added to 150 ml of N,N-dimethylformamide, followed by stirring under heating at 90° C. for 4 hours. After completion of the reaction, water was added to the reaction mixture, extraction with ethyl acetate was carried out, and the organic layer was dried over anhydrous magnesium sulfate. The solvent was distilled off under reduced pressure, and the obtained residue was purified by silica gel column chromatography (Wakogel C-200, eluent: hexane/ethyl acetate=3/1). The obtained crystals were washed with isopropyl ether to obtain 6.0 g of methyl N-(2-chloro-5-acetylbenzyl)carbamate as colorless crystals.

$^1$H-NMR: (CDCl$_3$/TMS, δ (ppm)); 2.59 (s, 3H); 3.70 (s, 3H); 4.50 (d, 2H); 5.31 (br, 1H); 7.46 (d, 1H); 7.81 (dd, 1H); 7.97 (s, 1H).

The agricultural/horticultural fungicides of the present invention contain carbamate derivatives represented by the general formula [I] as the active ingredients. When the compounds of the present invention are used for agricultural/horticultural fungicides, the active ingredient can be used in appropriate formulations depending on the purpose. The active ingredient is usually diluted with an inert liquid or solid carrier and is used in an appropriate dosage form such as a dust, a wettable powder, an emulsifiable concentrate or a granule by blending it with a surfactant and other ingredients, depending on its use. The blending proportion of the active ingredient is suitably selected depending on the case. However, preferable proportion is from 0.1 to 20% (by weight) in the cases of a dust or a granule, and from 5 to 80% (by weight) in the cases of an emulsifiable concentrate or a wettable powder.

Preferable examples of carriers include solid carriers such as talc, bentonite, clay, kaolin, diatomaceous earth, white carbon, vermiculite, slaked lime, silica sand, ammonium sulfate and urea and liquid carriers such as isopropyl alcohol, xylene, cyclohexanone and methylnaphthalene. Examples of surfactants and dispersants include dinaphthylmethanesulfonates, alcohol-sulfuric acid ester salts, alkylarylsulfonates, lignin sulfonate, polyoxyethylene glycol ether, polyoxyethylene alkyl aryl ethers and polyoxyethylene sorbitan monoalkylate. Examples of adjuvants include carboxymethyl cellulose and the like.

The agricultural/horticultural fungicides of the present invention are applied after these formulations are diluted or directly for foliage treatment, seed treatment, soil treatment, paddy water application or nursery box treatment. The dose depends on the type of the compound to be used, the disease to be controlled, the tendency of disease development, the degrees of the damage, the environmental conditions, the type of the formulation to be used and the like. For example, for direct use as a dust or a granule, the dose of the active ingredient is selected suitably within a range of from 0.1 g to 5 kg, preferably from 1 g to 1 kg, per 10 are. For use in a liquid state as an emulsifiable concentrate or a wettable powder, the dose is selected suitably within a range of from 0.1 ppm to 10,000 ppm, preferably from 10 to 3,000 ppm.

The compound of the present invention in the above formulations can control plant diseases caused by Oomycetes, Ascomycetes, Basidiomycetes and Deuteromycetes. Specific but non-restrictive examples of microorganisms are given below. Pseudoperonospora genus such as *Pseudoperonospora cubensis*, Venturia genus such as *Venturia inaequalis*, Erysiphe genus such as *Erysiphe graminis*, Pyricularia genus such as *Pyricularia oryzae*, Botrytis genus such as *Botrytis cinerea*, Rhizoctonia genus such as *Rhizoctonia solani*, Puccinia genus such as *Puccinia recondita*, Septoria genus such as *Septoria nodorum*, and Sclerotinia such as *Sclerotinia sclerotiorum*.

The compounds of the present invention can be used in combination with insecticides, other fungicides, herbicides, plant growth regulators or fertilizers, as the case requires. Now, typical formulations of the agricultural/horticultural fungicides of the present invention will be described with reference to Formulation Examples. Hereinafter, "%" means "% by weight".

Formulation Example 1

Dust

2% of Compound (A-30), 5% of diatomaceous earth and 93% of clay were uniformly mixed and pulverized to give a dust.

Formulation Example 2

Wettable Powder

50% of Compound (A-31), 45% of diatomaceous earth, 2% of sodium dinaphthylmethanedisulfonate and 3% of sodium lignin sulfonate were uniformly mixed and pulverized to give a wettable powder.

Formulation Example 3

Emulsifiable Concentrate

30% of Compound (A-109), 20% of cyclohexanone, 11% of polyoxyethylene alkyl aryl ether, 4% of calcium alkylbenzenesulfonate and 35% of methylnaphthalene were uniformly dissolved to give an emulsifiable concentrate.

Formulation Example 4

Granule

5% of Compound (A-45), 2% of sodium salt of lauryl alcohol sulfuric ester, 5% of sodium lignin sulfonate, 2% of carboxymethyl cellulose and 86% of clay were uniformly mixed and pulverized. The resulting mixture was kneaded with 20% of water, granulated to 14 to 32 mesh by means of an extrusion granulator and dried to give a granule.

Now, the effects of the agricultural/horticultural fungicides of the present invention will be described with reference to specific Test Examples.

Test Example 1

Test for Preventive Effect on Wheat Powdery Mildew

10 Wheat seeds (variety: Norin-61-go) were sown in each plastic pot having a diameter of 6 cm, and grown in a greenhouse. Wheat seedlings which reached a two-leaf stage were treated with 10 ml per pot of aqueous solutions of wettable powders prepared in accordance with Formulation Example 2, at a concentration of 500 ppm in terms of the active ingredients, and dried in the air. Then, the seedlings were inoculated with *Erysiphe graminis* spore and controlled in a greenhouse. 10 Days after the inoculation, the total diseased area of the first leaves in each pot was observed and evaluated on the basis of the standards shown in Table 21. The results are shown in Table 22.

TABLE 21

| Evaluation | |
|---|---|
| A | No diseased area |
| B | Diseased area of less than 5% |
| C | Diseased area of at least 5% but less than 10% |
| D | Diseased area of at least 10% |

TABLE 22

| Compound No. | Evaluation |
|---|---|
| A-3 | A |
| A-30 | B |
| A-31 | B |
| A-37 | A |
| A-38 | A |
| A-39 | A |
| A-40 | A |
| A-41 | B |
| A-42 | A |
| A-43 | A |
| A-46 | A |
| A-49 | A |
| A-50 | A |
| A-51 | A |
| A-55 | A |
| A-58 | A |
| A-61 | A |
| A-62 | A |
| A-64 | B |
| A-80 | A |
| A-81 | A |
| A-82 | A |
| A-83 | A |
| A-84 | A |
| A-85 | A |
| A-86 | A |
| A-87 | A |
| A-88 | A |
| A-89 | A |
| A-90 | A |
| A-91 | A |
| A-92 | A |
| A-98 | A |
| A-99 | A |
| A-100 | A |
| A-101 | A |
| A-112 | A |
| A-113 | A |

Test Example 2

Test for Preventive Effect on Septoria Leaf Blotch of Wheat

10 Wheat seeds (variety: Norin-61-go) were sown in each plastic pot having a diameter of 6 cm, and grown in a greenhouse. Wheat seedlings which reached a two-leaf stage were treated with 10 ml per pot of aqueous solutions of wettable powders prepared in accordance with Formulation Example 2, at a concentration of 50 ppm in terms of the active ingredients, and dried in the air. Then, the seedlings were inoculated with *Septoria nodorum* pycnidia and controlled in a greenhouse. 10 Days after the inoculation, the total diseased area of the first leaves in each pot was observed and evaluated on the basis of the standards shown in Table 21. The results are shown in Table 23.

TABLE 23

| Comp. No. | Evaluation | Comp. No. | Evaluation | Comp. No. | Evaluation | Comp. No. | Evaluation | Comp. No. | Evaluation |
|---|---|---|---|---|---|---|---|---|---|
| A-3 | B | A-153 | A | A-291 | A | A-346 | A | A-398 | A |
| A-7 | A | A-154 | A | A-293 | A | A-347 | A | A-400 | B |
| A-8 | B | A-155 | A | A-294 | B | A-348 | B | A-403 | A |
| A-20 | B | A-156 | A | A-295 | B | A-349 | A | A-404 | A |
| A-21 | A | A-157 | A | A-296 | A | A-354 | B | A-405 | A |
| A-51 | B | A-158 | A | A-297 | B | A-355 | B | A-406 | A |
| A-52 | A | A-159 | A | A-303 | A | A-356 | A | A-407 | A |
| A-53 | A | A-160 | B | A-304 | A | A-358 | A | A-410 | A |
| A-54 | A | A-185 | A | A-305 | A | A-359 | B | A-411 | A |
| A-56 | B | A-189 | A | A-306 | A | A-360 | A | A-412 | A |
| A-58 | B | A-198 | A | A-309 | B | A-361 | B | A-413 | A |
| A-61 | B | A-201 | A | A-310 | A | A-362 | A | A-414 | A |
| A-62 | B | A-206 | B | A-311 | A | A-363 | A | A-415 | A |
| A-64 | A | A-207 | A | A-312 | A | A-364 | A | A-416 | A |
| A-70 | A | A-208 | B | A-313 | A | A-365 | B | A-417 | A |
| A-73 | A | A-215 | A | A-314 | A | A-367 | A | A-418 | A |
| A-80 | A | A-216 | A | A-315 | A | A-368 | A | A-428 | A |
| A-81 | B | A-217 | A | A-320 | A | A-369 | A | A-429 | A |
| A-82 | B | A-218 | A | A-321 | B | A-370 | A | A-430 | A |
| A-83 | A | A-220 | A | A-322 | A | A-371 | A | A-431 | A |
| A-85 | B | A-225 | A | A-323 | A | A-372 | A | A-432 | A |
| A-87 | B | A-227 | B | A-324 | A | A-373 | A | A-433 | B |
| A-88 | B | A-228 | B | A-325 | A | A-374 | A | A-438 | B |
| A-89 | B | A-241 | B | A-326 | A | A-375 | B | A-440 | B |
| A-90 | A | A-242 | A | A-327 | A | A-376 | B | A-441 | A |
| A-91 | B | A-248 | B | A-328 | A | A-377 | A | A-443 | B |
| A-92 | B | A-251 | A | A-329 | A | A-378 | A | A-444 | B |
| A-93 | A | A-252 | A | A-330 | B | A-379 | A | | |
| A-94 | A | A-254 | A | A-331 | A | A-380 | A | | |
| A-95 | A | A-256 | A | A-332 | A | A-381 | A | | |
| A-98 | A | A-257 | A | A-333 | A | A-382 | B | | |
| A-99 | B | A-258 | B | A-334 | A | A-384 | A | | |

TABLE 23-continued

| Comp. No. | Evaluation | Comp. No. | Evaluation | Comp. No. | Evaluation | Comp. No. | Evaluation | Comp. No. | Evaluation |
|---|---|---|---|---|---|---|---|---|---|
| A-102 | A | A-266 | B | A-338 | A | A-385 | B | | |
| A-103 | B | A-269 | A | A-339 | A | A-386 | B | | |
| A-111 | A | A-277 | B | A-340 | B | A-387 | B | | |
| A-112 | B | A-278 | B | A-341 | A | A-388 | A | | |
| A-113 | A | A-279 | B | A-342 | A | A-389 | A | | |
| A-150 | B | A-283 | B | A-343 | A | A-392 | A | | |
| A-151 | A | A-285 | A | A-344 | A | A-396 | A | | |
| A-152 | A | A-286 | A | A-345 | B | A-397 | A | | |

Test Example 3

Test for Preventive Effect on Cucumber Gray Mold 4 cucumber seeds (variety: Sagami-hanziro) were sown in each plastic pot having a diameter of 6 cm and grown in a greenhouse. Cucumber young seedlings which reached a cotyledon stage were treated with 10 ml per pot of aqueous solutions of wettable powders prepared in accordance with Formulation Example 2, at a concentration of 500 ppm in terms of the active ingredients and dried in the air. Then, the seedlings were inoculated with *Botrytis cinerea* spore by putting a paper disc soaked with the spore suspension on the surface of the cucumber cotyledons, and the seedlings were immediately placed in a moist chamber of 22° C. 3 Days after the inoculation, the total diseased area of the cotyledons in each pot was observed and evaluated on the basis of the standards shown in Table 24. The results are shown in Table 25.

TABLE 24

| | Evaluation |
|---|---|
| A | No diseased area |
| B | Diseased area of less than 25% of the non-treated plot |
| C | Diseased area of at least 25% but less than 50% of the non-treated plot |
| D | Diseased area of at least 50% |

TABLE 25

| Comp. No. | Evaluation |
|---|---|
| A-3 | B |
| A-7 | B |
| A-37 | B |
| A-38 | A |
| A-39 | B |
| A-40 | B |
| A-46 | B |
| A-49 | B |
| A-50 | A |
| A-51 | A |
| A-62 | B |
| A-81 | A |
| A-82 | B |
| A-83 | B |
| A-84 | B |
| A-87 | B |
| A-88 | B |
| A-90 | B |
| A-99 | B |
| A-100 | B |
| A-112 | A |
| A-113 | B |
| A-150 | B |

TABLE 25-continued

| Comp. No. | Evaluation |
|---|---|
| A-157 | B |
| A-206 | B |
| A-220 | B |
| A-225 | B |
| A-254 | B |
| A-255 | B |
| A-256 | B |
| A-258 | B |
| A-279 | B |
| A-285 | B |
| A-286 | A |
| A-291 | 3 |
| A-294 | A |
| A-295 | B |
| A-296 | A |
| A-297 | B |
| A-300 | B |
| A-305 | B |
| A-306 | A |
| A-309 | A |
| A-310 | B |
| A-311 | B |
| A-312 | B |
| A-313 | A |
| A-314 | A |
| A-315 | A |
| A-322 | B |
| A-323 | A |
| A-324 | A |
| A-325 | A |
| A-326 | A |
| A-327 | B |
| A-328 | A |
| A-329 | B |
| A-330 | A |
| A-331 | B |
| A-333 | B |
| A-334 | B |
| A-338 | B |
| A-341 | B |
| A-342 | B |
| A-343 | B |
| A-348 | A |
| A-355 | A |
| A-363 | B |
| A-367 | B |
| A-370 | A |
| A-371 | B |
| A-373 | B |
| A-375 | A |
| A-377 | A |
| A-384 | B |
| A-396 | A |
| A-404 | B |
| A-405 | B |
| A-406 | B |
| A-407 | A |
| A-410 | B |
| A-412 | A |

TABLE 25-continued

| Comp. No. | Evaluation |
|---|---|
| A-413 | A |
| A-415 | A |
| A-416 | B |
| A-417 | A |
| A-420 | A |
| A-424 | A |
| A-425 | A |
| A-427 | A |
| A-428 | B |
| A-429 | A |
| A-430 | A |
| A-432 | B |
| A-437 | B |
| A-438 | B |
| A-443 | B |

INDUSTRIAL APPLICABILITY

The agricultural/horticultural fungicides of the present invention have high controlling effects on cucumber downy mildew, apple scab, wheat powdery mildew, rice blast, cucumber gray mold, rice sheath blight, wheat brown leaf rust, wheat septoria leaf blotch and cucumber stem rot, and are excellent in residual effectiveness and rain-fastness without damaging crops, and thus they are useful as agricultural/horticultural fungicides.

What is claimed is:

1. A carbamate compound represented by formula [I]:

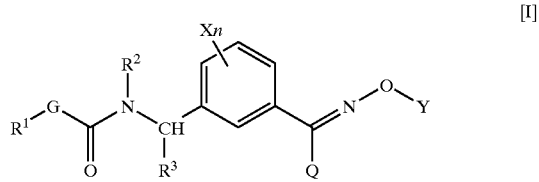

wherein X is a halogen atom, a $C_1$–$C_6$ alkyl group, a $C_1$–$C_6$ alkoxy group, a $C_1$–$C_6$ haloalkyl group or a $C_3$–$C_6$ haloalkoxy group, n is 0 or an integer of from 1 to 4, $R^1$ is a $C_1$–$C_6$ alkyl group, $R^2$ is a hydrogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $C_1$–$C_6$ alkylcarbonyl group, a $C_1$–$C_6$ alkoxycarbonyl group, a $C_1$–$C_6$ alkylcarbonyl $C_1$–$C_6$ alkyl group or a benzyl group which may be substituted, $R^3$ is a hydrogen atom or a $C_1$–$C_6$ alkyl group, G is an oxygen atom, a sulfur atom or a —$NR^4$— group, wherein $R^4$ is a hydrogen atom or a $C_1$–$C_6$ alkyl group, Y is a hydrogen atom, a $C_1$–$C_{10}$ alkyl group said group may be which is optionally substituted by the same or different at least one halogen atom, cyano group, nitro group, hydroxyl group, $C_3$–$C_6$ cycloalkyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ alkylsulfinyl group, carboxyl group, $C_1$–$C_6$ alkylcarbonyl group, $C_1$–$C_6$ alkoxycarbonyl group, $C_1$–$C_6$ alkoxyimino group, or $C(O)NR^5R^6$, wherein each of $R^5$ and $R^6$ which are the same or different, is a hydrogen atom or a $C_1$–$C_6$ alkyl group, a $C_2$–$C_{10}$ alkenyl group which is optionally substituted by the same or different at least one halogen atom, cyano group, nitro group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group, a $C_2$–$C_{10}$ alkynyl group which is optionally substituted by the same or different at least one halogen atom, cyano group, nitro group, cycloalkyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^3R^6$, wherein each of $R^5$ and $R^6$ which are the same or different, is a hydrogen atom or a $C_1$–$C_6$ alkyl group, a $C_3$–$C_6$ cycloalkyl group which is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group, a $C_3$–$C_6$ cycloalkenyl group which is optionally substituted by the same or different at least one halogen atom, cyano group, nitro group, $C_1$–$C_6$ alkyl group, $C_2$–$C_6$ alkenyl group, hydroxyl group, $C_2$–$C_6$ alkynyl group, amino group, mono $C_1$–$C_6$ alkylamino group, di-$C_1$–$C_6$ alkylamino group, $C_1$–$C_6$ alkoxy group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group, a phenacyl group which is optionally substituted by the same or different at least one halogen atom, $C_1$–$C_6$ alkyl group, $C_1$–$C_6$ alkoxy group, $C_1$–$C_6$ haloalkyl group, $C_1$–$C_6$ alkylcarbonyl group or $C_1$–$C_6$ alkoxycarbonyl group, an aryl group which is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group, a heteroaryl group which is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group, an aryl-$C_1$–$C_6$ alkyl group, wherein the aryl in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, phenoxy group which may be substituted, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ haloalkoxy group, $C_1$–$C_6$ alkylcarbonyl group, $C_1$–$C_6$ alkoxycarbonyl group, $C_1$–$C_6$ alkoxyimino $C_1$–$C_6$ alkyl group, or $C(O)NR^5R^6$, wherein each of $R^5$ and $R^6$ which are the same or different, and is a hydrogen atom or a $C_1$–$C_6$ alkyl group, an aryl-$C_1$–$C_6$ alkenyl group wherein the aryl in said group is optionally substituted by the same or different at least one halogen atom, cyano group, nitro group, $C_1$–$C_6$ alkyl group, $C_1$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$ which are the same or different, is a hydrogen atom or a $C_1$–$C_6$ alkyl group or a heterocyclic-$C_1$–$C_6$ alkyl group wherein the heterocycle in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$ which are the same or different, is a hydrogen atom or a $C_1$–$C_6$ alkyl group, and Q is a hydrogen atom, a haloalkyl group, a cyano group, a $C_1$–$C_6$ alkyl group, a $C_3$–$C_6$ cycloalkyl group, a $C_1$–$C_4$ alkylthio group, a $C_1$–$C_4$ alkylsulfinyl group, a $C_1$–$C_4$ alkylsulfonyl group or a phenyl group, wherein said group is optionally substituted by at least one halogen atom, cyano group, nitro group, $C_1$–$C_4$ alkyl group, $C_2$–$C_4$ alkenyl group, $C_2$–$C_4$ alkynyl group, hydroxyl group, $C_1$–$C_4$ alkoxy group, $C_1$–$C_4$ haloalkyl group, $C_1$–$C_4$ haloalkoxy group, $C_1$–$C_4$ alkylcarbonyl group or $C_1$–$C_4$ alkoxycarbonyl group.

2. The carbamate compound according to claim 1, wherein Y is a hydrogen atom, a substituted $C_1$–$C_{10}$ alkyl group which is substituted by the same or different at least one halogen atom, cyano group, nitro group, hydroxyl group, $C_3$–$C_6$ cycloalkyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ alkylsulfinyl group, carboxyl group, $C_1$–$C_6$ alkylcarbonyl group, $C_1$–$C_6$ alkoxycarbonyl group, $C_1$–$C_6$ alkoxyimino group, or C(O)NR$^5$R$^6$, wherein each of R$^5$ and R$^6$ which are the same or different, is a hydrogen atom or a $C_1$–$C_6$ alkyl group, a $C_2$–$C_{10}$ alkenyl group, wherein said group is optionally substituted by the same or different at least one halogen atom, cyano group, nitro group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$, which are the same or different, is a hydrogen atom or a $C_1$–$C_6$ alkyl group, a $C_2$–$C_{10}$ alkynyl group wherein said group is optionally substituted by the same or different at least one halogen atom, cyano group, nitro group, cycloalkyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$, which are the same or different, is a hydrogen atom or a $C_1$–$C_6$ alkyl group, a $C_3$–$C_6$ cycloalkyl group, wherein said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$ which are the same or different, is a hydrogen atom or a $C_1$–$C_6$ alkyl group, a $C_3$–$C_6$ cycloalkenyl group, wherein said group is optionally substituted by the same or different at least one halogen atom, cyano group, nitro group, $C_1$–$C_6$ alkyl group, $C_2$–$C_6$ alkenyl group, hydroxyl group, $C_2$–$C_6$ alkynyl group, amino group, mono $C_1$–$C_6$ alkylamino group, di-$C_1$–$C_6$ alkylamino group, $C_1$–$C_6$ alkoxy group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$ which are the same or different, is a hydrogen atom or a $C_1$–$C_6$ alkyl group, a phenacyl group, wherein said group is optionally substituted by the same or different at least one halogen atom, $C_1$–$C_6$ alkyl group, $C_1$–$C_6$ alkoxy group, $C_1$–$C_6$ haloalkyl group, $C_1$–$C_6$ alkylcarbonyl group or $C_1$–$C_6$ alkoxycarbonyl group, an aryl group, wherein said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$ which are the same or different, is a hydrogen atom or a $C_1$–$C_6$ alkyl group, a heteroaryl group, wherein said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$ which are the same or different, is a hydrogen atom or a $C_1$–$C_6$ alkyl group, an aryl-$C_1$–$C_6$ alkyl group, wherein the aryl in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, phenoxy group which may be substituted, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ haloalkoxy group, $C_1$–$C_6$ alkylcarbonyl group, $C_1$–$C_6$ alkoxycarbonyl group, $C_1$–$C_6$ alkoxyimino $C_1$–$C_6$ alkyl group, or C(O)NR$^5$R$^6$, wherein each of R$^5$ and R$^6$ which are the same or different, is a hydrogen atom or a $C_1$–$C_6$ alkyl group, an aryl-$C_2$–$C_6$ alkenyl group, wherein the aryl in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$ which are the same or different, is a hydrogen atom or a $C_1$–$C_6$ alkyl group or a heterocyclic-$C_1$–$C_6$ alkyl group, wherein the heterocycle in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$ which are the same or different, is a hydrogen atom or a $C_1$–$C_6$ alkyl group.

3. The carbamate compound according to claim 1, wherein Y is a hydrogen atom, a $C_2$–$C_{10}$ alkenyl group, wherein said group is optionally substituted by the same or different at least one halogen atom, cyano group, nitro group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or C(O)NR$^5$R$^6$, wherein each of R$^5$ and R$^6$ which are the same or different, is a hydrogen atom or a $C_1$–$C_6$ alkyl group, a $C_2$–$C_{10}$ alkynyl group, wherein said group is optionally substituted by the same or different at least one halogen atom, cyano group, nitro group, cycloalkyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or $C(O)NR^5R^6$ wherein each of $R^5$ and $R^6$ which are the same or different, is a hydrogen atom or a $C_1$–$C_6$ alkyl group, a $C_3$–$C_6$ cycloalkyl group, wherein said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group, a $C_3$–$C_6$ cycloalkenyl group, said group is optionally substituted by the same or different at least one halogen atom, cyano group, nitro group, $C_1$–$C_6$ alkyl group, $C_2$–$C_6$ alkenyl group, hydroxyl group, $C_2$–$C_6$ alkynyl group, amino group, mono $C_1$–$C_6$ alkylamino group, di-$C_1$–$C_6$ alkylamino group, $C_1$–$C_6$ alkoxy group, $C_1$–$C_6$ alkylthio group, $C_1$–$C_6$ haloalkyl group, $C_1$–$C_6$ alkylcarbonyl group, $C_1$–$C_6$ alkoxycarbonyl group or $C(O)NR^5R^6$, wherein each of $R^5$ and $R^6$ which are the same or different, is a hydrogen atom or a $C_1$–$C_6$ alkyl group, a phenacyl group, wherein said group is optionally substituted by the same or different at least one halogen atom, $C_1$–$C_6$ alkyl group, $C_1$–$C_6$ alkoxy group, $C_1$–$C_6$ haloalkyl group, $C_1$–$C_6$ alkylcarbonyl group or $C_1$–$C_6$ alkoxycarbonyl group, an aryl group, wherein said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group, a heteroaryl group, wherein said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group, an aryl-$C_1$–$C_6$ alkyl group, wherein the aryl in said group is optionally substituted by the same or different at least one halogen atom, cyano group, nitro group, $C_1$–$C_6$ alkyl group, $C_2$–$C_6$ alkenyl group, $C_1$–$C_6$ alkynyl group, phenoxy group which is optionally substituted, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ haloalkoxy group, $C_1$–$C_6$ alkylcarbonyl group, $C_1$–$C_6$ alkoxycarbonyl group, $C_1$–$C_6$ alkoxyimino $C_1$–$C_6$ alkyl group, or $C(O)NR^5R^6$, wherein each of $R^5$ and $R^6$ which are the same or different, is a hydrogen atom or a $C_1$–$C_6$ alkyl group, an aryl-$C_2$–$C_6$ alkenyl group wherein the aryl in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group or a heterocyclic-$C_1$–$C_6$ alkyl group the heterocycle in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or $C(O)NR^5R^6$, wherein each of $R^5$ and $R^6$ which are the same or different, is a hydrogen atom or a $C_1$–$C_6$ alkyl group.

4. The carbamate compound according to claim 1, wherein Y is an aryl-$C_1$–$C_6$ alkyl group, wherein the aryl in said group may be substituted by the same or different at least one halogen atom, cyano group, nitro group, $C_1$–$C_6$ alkyl group, $C_2$–$C_6$ alkenyl group, $C_2$–$C_6$ alkynyl group, phenoxy group which is optionally substituted, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ haloalkoxy group, $C_1$–$C_6$alkylcarbonyl group, $C_1$–$C_6$ alkoxycarbonyl group, $C_1$–$C_6$ alkoxyimino $C_1$–$C_6$ alkyl group, or $C(O)NR^5R^6$, wherein each of $R^5$ and $R^6$ which are the same or different, is a hydrogen atom or a $C_1$–$C_6$ alkyl group.

5. The carbamate compound according to claim 1, wherein Y is a heterocyclic-$C_1$–$C_6$ alkyl group, wherein the heterocycle in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group.

6. The carbamate compound according to claim 1, wherein Y is a heteroaryl-$C_1$–$C_6$ alkyl group, wherein the heteroaryl in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group, or $C(O)NR^5R^6$, wherein each of $R^5$ and $R^6$ which are the same or different, is a hydrogen atom or a $C_1$–$C_6$ alkyl group.

7. The carbamate compound according to claim 1, wherein Y is a benzyl group, wherein said group is optionally substituted by the same or different at least one halogen atom, cyano group, nitro group, $C_1$–$C_6$ alkyl group, $C_2$–$C_6$ alkenyl group, $C_2$–$C_6$ alkynyl group, phenoxy group which is optionally substituted, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ haloalkoxy group, $C_1$–$C_6$ alkylcarbonyl group, $C_1$–$C_6$ alkoxycarbonyl group, $C_1$–$C_6$ alkoxyimino $C_1$–$C_6$ alkyl group, or $C(O)NR^5R^6$, wherein each of $R^5$ and $R^6$ which are the same or different, is a hydrogen atom or a $C_1$–$C_6$ alkyl group or a heteroaryl-$C_1$–$C_6$ alkyl group represented by a five- to six-membered cycle containing at least one nitrogen atom wherein the heteroaryl in said group is optionally substituted by the same or different at least one halogen atom, cyano group, nitro group, $C_1$–$C_6$ alkyl group, $C_2$–$C_6$ alkenyl group, $C_2$–$C_6$ alkynyl group, hydroxyl group, $C_1$–$C_6$ alkoxy group, amino group, mono $C_1$–$C_6$ alkylamino group, di-$C_1$–$C_6$ alkylamino group, $C_1$–$C_6$ alkylthio group, $C_1$–$C_6$ haloalkyl group, $C_1$–$C_6$ alkylcarbonyl group, $C_1$–$C_6$ alkoxycarbonyl group or C(O)NR$^5$R$^6$, wherein each of R$^5$ and R$^6$ which are the same or different, is a hydrogen atom or a $C_1$–$C_6$ alkyl group.

8. An agricultural/horticultural fungicide composition, comprising:

the carbamate derivative as defined claim 1 as the active ingredient and a fungicidally acceptable carrier.

9. The agricultural/horticultural fungicide composition according to claim 8, wherein the composition, formulated as a dust or granules, contains from 0.1 to 20% by weight of the active ingredient.

10. The agricultural/horticultural fungicide composition according to claim 8, wherein the composition, formulated as an emulsifiable concentrate or a wettable powder, contains from 5 to 80% by weight of the active ingredient.

11. The agricultural/horticultural fungicide composition according to claim 8, wherein the carrier is a solid carrier selected from the group consisting of talc, bentonite, clay, kaolin, diatomaceous earth, white carbon, vermiculite, slaked lime, silica sand, ammonium sulfate and urea.

12. The agricultural/horticultural fungicide composition according to claim 8, wherein the carrier is a liquid carrier selected from the group consisting of isopropyl alcohol, xylene, cyclohexanone and methylnaphthalene.

13. The agricultural/horticultural fungicide composition according to claim 8, wherein the composition is formulated with a surfactant or dispersant selected from the group consisting of dinaphthylmethanesulfonate, alcohol sulfuric acid ester salts, alkylarylsulfonates, lignin sulfonate, polyoxyethylene glycol ether, polyoxyethylene alkyl aryl ether and polyoxyethylene sorbitan monoalkylate.

* * * * *